(12) United States Patent  
Kvaløy et al.

(10) Patent No.: US 12,383,432 B2
(45) Date of Patent: Aug. 12, 2025

(54) HEARING PROTECTION DEVICE

(71) Applicant: MINUENDO AS, Oslo (NO)

(72) Inventors: Olav Kvaløy, Oslo (NO); Erik Swendgaard, Oslo (NO); Odd Kr. Ø Pettersen, Oslo (NO); Håkon Aurvik, Oslo (NO)

(73) Assignee: MINUENDO AS, Oslo (NO)

( * ) Notice: Subject to any disclaimer, the term of this patent is extended or adjusted under 35 U.S.C. 154(b) by 256 days.

(21) Appl. No.: 17/757,927

(22) PCT Filed: Dec. 22, 2020

(86) PCT No.: PCT/GB2020/053341
§ 371 (c)(1),
(2) Date: Jun. 23, 2022

(87) PCT Pub. No.: WO2021/130482
PCT Pub. Date: Jul. 1, 2021

(65) Prior Publication Data
US 2023/0021291 A1   Jan. 19, 2023

(30) Foreign Application Priority Data

Dec. 23, 2019  (GB) ..................................... 1919221
Aug. 21, 2020  (GB) ..................................... 2013084

(51) Int. Cl.
*A61F 11/08* (2006.01)

(52) U.S. Cl.
CPC .................................. *A61F 11/085* (2022.01)

(58) Field of Classification Search
CPC ........ A61F 11/085; A61F 11/08; A61F 11/06; A61F 11/10; A61F 11/12
See application file for complete search history.

(56) References Cited

U.S. PATENT DOCUMENTS 3,637,040 A  *  1/1972  Gorman .................. A61F 11/14
                                                   381/372
3,702,123 A  *  11/1972  Macken ............... H04R 25/652
                                                   381/328

(Continued)

FOREIGN PATENT DOCUMENTS

CN         106878878 A         5/2018
CN         107684488 A         8/2018

(Continued)

OTHER PUBLICATIONS

International Search Report and Written Opinion of the International Application No. PCT/GB2020/053341 mailed Apr. 20, 2021.

(Continued)

*Primary Examiner* — Camtu T Nguyen

(74) *Attorney, Agent, or Firm* — HESLIN, ROTHENBERG, FARLEY & MESITI, P.C.; George S. Blasiak, Esq.

(57) ABSTRACT

A device (1) for insertion into an ear canal of a mammalian subject. The device includes a body (2) having a sound path extending therethough and a tensioned membrane (10) in the sound path. The tensioned membrane has at least one corrugation (12). The device further includes an adjustable member (6) arranged to bear against the membrane to adjust the tension of the membrane and thereby to alter an acoustic response of the sound path. The adjustable member may include a compressible portion (8).

28 Claims, 13 Drawing Sheets

(56) References Cited

U.S. PATENT DOCUMENTS

| | | | |
|---|---|---|---|
| 5,332,871 A * | 7/1994 | Carrigan | A61F 11/08 181/135 |
| 5,631,965 A | 5/1997 | Chang et al. | |
| 7,240,765 B2 | 7/2007 | Berg et al. | |
| 7,478,702 B2 * | 1/2009 | Berg | B33Y 80/00 381/328 |
| 7,512,243 B2 * | 3/2009 | Haussmann | A61F 11/08 381/72 |
| 8,161,975 B2 | 4/2012 | Turdjian | |
| 9,253,556 B1 | 2/2016 | Pounds et al. | |
| 2012/0255564 A1 * | 10/2012 | Park | A61F 11/10 128/864 |
| 2014/0190494 A1 * | 7/2014 | Ely | A61F 11/08 128/868 |
| 2016/0022499 A1 * | 1/2016 | Brown | G10K 11/002 181/135 |
| 2018/0098885 A1 | 4/2018 | Delfino et al. | |
| 2018/0277087 A1 | 9/2018 | Van' T Hof et al. | |
| 2022/0168149 A1 * | 6/2022 | Kvaløy | A61F 11/085 |

FOREIGN PATENT DOCUMENTS

| | | |
|---|---|---|
| EP | 1276443 A1 | 1/2003 |
| GB | 2596981 A | 3/2020 |
| WO | WO 0176520 | 4/2001 |
| WO | 2008122093 A1 | 10/2008 |
| WO | WO 2013080005 | 11/2012 |
| WO | WO 2016010431 | 7/2015 |
| WO | WO 201203218 | 5/2017 |
| WO | 2017099600 A1 | 6/2017 |
| WO | WO 2018070876 | 10/2017 |
| WO | WO 2019194722 | 3/2019 |
| WO | WO 2020188298 A1 | 9/2020 |

OTHER PUBLICATIONS

China National Intellectual Property Administration, First Examination Opinion Notice, mailed Mar. 21, 2025. 24 pages (w/ translation).

List of Foreign References and Their Translations, dated Apr. 17, 2025. 2 pages.

* cited by examiner

HEARING PROTECTION DEVICE

CROSS REFERENCE TO RELATED APPLICATIONS

This application is a national stage filing under section 371 of International Application No. PCT/GB2020/053341 filed on Dec. 22, 2020, and published on Jul. 1, 2021 as WO2021/130482 A1, which claims priority to Great Britain Application Nos. 1919221.0 filed on Dec. 23, 2019 and to 2013084.5 filed on Aug. 21, 2020. The entire contents of WO2021/130482 A1 are hereby incorporated herein by reference.

The present invention relates to ear protection used, for example, to reduce the intensity of sounds experienced by a user.

Exposure to high intensity noises can cause damage to a person's hearing. The damaging effects are increased when a person is frequently exposed to loud noises. In extreme cases, frequent exposure to loud noises can cause noise-induced hearing loss. Therefore, in order to protect a person's hearing it is necessary to reduce the effects of loud noises. As a result of the increasing awareness of the damaging effects of loud noises, for example from industrial sources, there are now various industry requirements for personnel to use ear protection. There are many situations in which personnel may be exposed to loud noises, for example when operating loud machinery. A common form of noise protection widely used are earplugs; these reduce the intensity of the sound entering a person's ears and thus reduce the damaging effects of high intensity noises.

There are two main types of earplugs that are commonly used: passive earplugs and active earplugs. Passive earplugs attenuate the intensity of all levels of sound equally, i.e. they provide a uniform level of attenuation, regardless of the intensity of sound present, for example, a reduction of 20 dB. Passive earplugs come in various forms including: foam, silicon, flanged and custom moulded earplugs. Passive earplugs are typically inserted into a user's ear canal. Passive earplugs use the material of the earplug itself to attenuate the sound which passes through it. As the incident sound passes through the earplug, the sound is attenuated by the material of the earplug. Some sound will propagate through the earplug and pass out of the earplug into the air volume of the user's ear canal where it will be detected by the user. The intensity of the sound will be reduced and thus the risk of damage to the user's hearing may be reduced.

If they are inserted properly, the fixed level of attenuation provided by passive earplugs is relatively high. As a result, users of passive earplugs typically have to periodically remove them in order to be communicate orally with fellow workers.

The inconvenience associated with having to repeatedly remove and replace the earplugs, depending on the noise levels, may lead to reduced compliance with requirements to wear the earplugs in certain situations.

On the other hand, active earplugs often comprise a passive earplug used in conjunction with a microphone on the external side of the earplug and a speaker on the internal side of the earplug. Active earplugs typically listen to the sound on the outside of the earplug, and then replay it to a user via the speaker at a reduced intensity. Active earplugs can employ control circuitry to apply different levels of attenuation at different times or different frequencies—known as 'adaptive attenuation'. Some other systems contain circuitry that detects the incident sound and produces an out-of-phase signal that destructively interferes with the incident sound thus reducing the intensity of the incident sound as it propagates into the user's ear canal—this is often known as 'active noise cancelling'. One of the disadvantages of active earplugs is that they are often relatively expensive due to their electrical components. Additionally, active earplugs often have a relatively high power consumption due to the need to constantly monitor and replay detected sound.

The present invention seeks to address or mitigate the problems outlined above and according to a first aspect there is provided a device, for insertion into an ear canal of a mammalian subject, comprising:

a body, having a sound path extending therethrough;
a tensioned membrane in the sound path comprising at least one corrugation; and
an adjustable member arranged to bear against the membrane to adjust the tension of the membrane and thereby to alter an acoustic response of the sound path.

With the claimed arrangement of the tensioned membrane and the adjustable member, it is possible to control the sound passing through the sound path, e.g. the attenuation of the sound. By attenuating the sound, the device may reduce the intensity of sounds and therefore may help to reduce the risk of damage to an individual's hearing. This is because when the device is inserted into the ear canal of an individual, the sound is attenuated by the device so that the sound which propagates through the earplug and passes out of the earplug into the air volume of the user's ear canal (and reaching the user's eardrum) has a lower amplitude, than the sound which would propagate in the air volume of the user's ear canal if the device was not inserted.

Attenuation of sound provided by the device may be adjusted by altering the tension of the membrane. The force with which the adjustable member bears on the membrane may be adjusted to alter the tension of the membrane therefore changing the attenuation of sound by the device. This allows the level of attenuation of sound provided by the device to be varied. For example, an individual using the device may reduce the level of attenuation of sound provided by the device in order to communicate orally with fellow workers or an individual using the device may increase the level of attenuation of sound provided by the device upon entering an environment with higher amplitude noises.

It has further been appreciated by the Applicant that without the corrugation referred to, the level of attenuation provided by the device would increase substantially when the adjustable member first contacts the membrane compared to the level of attenuation provided when the adjustable member was not in contact with the adjustable membrane and would increase rapidly thereafter, even with small movements. The Applicant has appreciated that it would be desirable to be able to vary the level of attenuation provided more smoothly (e.g. with no large changes in the level of attenuation provided) and more gradually, to allow finer control over the attenuation provided by the device.

The Applicant has further appreciated that such finer control over the attenuation provided by the device can be achieved by implementing a tensioned membrane that includes at least one corrugation. When the adjustable member contacts the membrane, the corrugation is typically (at least partially) stretched due to the force the adjustable member exerts on the membrane and a smaller increase in the tension of the membrane may be observed for a given applied force. Therefore, the level of attenuation provided by the device may increase more gradually when the adjustable member contacts the membrane compared to a membrane without any corrugation.

In a set of embodiments, the corrugation comprises a ridge. In a potentially overlapping set of embodiments, the corrugation comprises an indentation. Depending on the orientation of the membrane, an identical corrugation could be described as either a ridge or an indentation. Preferably the maximum height of the ridge above or depth of the indentation below the plane of the membrane is in the range of 0.02 mm to 2 mm e.g. 0.1 mm to 1 mm e.g. 0.3 mm.

In a set of embodiments, the corrugation is arranged on the adjustable membrane such that the adjustable member does not contact the corrugation. The adjustable member may deform the corrugation by applying a force to another part of the membrane which is transmitted to the corrugation.

In a set of embodiments, the adjustable member is arranged to contact the membrane in the geometric centre of the membrane. In embodiments wherein the membrane is circular, the corrugation may be arranged on the membrane at a distance from the geometric centre of the membrane in the range of 30% to 90% of the radius of the membrane.

In a set of embodiments, the corrugation is circular and centred on the geometric centre of the membrane.

In a set of embodiments, the adjustable membrane comprises a plurality of corrugations. Different corrugations, or different subsets of the corrugations within the plurality of corrugations, may have different shapes and sizes. However, the plurality of corrugations may all have the same shape.

The Applicant has envisaged a particular arrangement in which the plurality of corrugations comprises a subset of circular ridges and subset of circular indentations, which may be centred on the geometric centre of the membrane. The various circular indentations and ridges would have various diameters, and therefore could be arranged at various distances (i.e. locations) from the geometric centre of the adjustable membrane.

Each circular ridge or indentation may be described as a wave. These waves are preferably connected such that there are no abrupt changes in the curvature of the membrane creating points of increased stress. This may be achieved by the circular indentations and ridges being arranged to alternate, e.g. if the innermost circular corrugation is an indentation/negative wave, the second innermost circular corrugation is a ridge/positive wave, the third innermost circular corrugation is an indentation/negative wave etc. In a set of embodiments, the centre of the membrane is flat.

Whilst the membrane may comprise any number of waves, in a set of embodiments the membrane comprises at least three waves. Preferably the membrane has three waves. In a particular set of embodiments, the innermost wave and outmost waves are 'positive' waves extending higher than the centre of the membrane (i.e. towards the direction of incidence of sound in use), and the intervening wave is a 'negative' wave extending lower than the centre of the membrane (i.e. away from the direction of incidence of sound during use). When sound is incident on the membrane and the adjustable member contacts the membrane, the positive waves may act as 'hinges' to generate movement of the intervening negative wave.

In embodiments in which the membrane comprises a plurality of waves, the dimensions of the waves may vary. For example, the height above or below the centre of the membrane, and/or the radial extent (width) of each wave may vary. In some embodiments, the height and the radial extent (width) of a wave may depend on the distance (i.e. location) of the wave from the geometric centre of the membrane. However the height of each wave and the width of each wave may be the same.

A wave may have a uniform cross-section section throughout the circumference of the circle formed. However, this is not essential and indeed the Applicant has appreciated that it may be beneficial that waves do not have a uniform cross-section. More particularly in a set of embodiments, the or each wave comprises a plurality of circumferentially spaced perturbations or 'ripples' thereon. Such perturbations may reduce the stress in the wave and allow the wave to move more freely when subjected to vibrations, such that the level of attenuation can be changed more smoothly and gradually to allow finer control over the attenuation provided by the device.

The number of perturbations on a given wave may be chosen to suit the application. In a set of embodiments, the number of perturbations on the or each wave is in the range 5 to 40, e.g. 10 to 30, e.g. 20.

The perturbations may be arranged in any suitable and desirable manner. Preferably the perturbations are evenly spaced around the circumference of the or each wave.

In a set of embodiment, the perturbations extend in an opposite direction to the corresponding wave on which they are formed—i.e. they appear as indentations on a wave when from viewed from above which extend towards the tangential plane of the centre of the membrane. Alternatively however the perturbations may project proud of the corresponding wave—i.e. extend further away from the tangential plane of the centre of the membrane.

Whilst the perturbations may extend radially, preferably the perturbations are non-radial. In such embodiments, the perturbations may be angled with respect to the radius of the membrane. In a set of embodiments, the angle between perturbations and the radius of the membrane is in the range of 5° to 85°, e.g. 20° to 70°, e.g. 45°.

In embodiments comprising a plurality of waves, one or more of the waves may comprise perturbations. It is preferable that every wave comprises perturbations. Whilst perturbations may be arranged to extend continuously across more than one wave, preferably adjacent waves comprises discrete sets of perturbations.

Different orientations of the perturbations with respect to the radius of the membrane may be provided on different waves, e.g. negative and positive waves may comprise perturbations with different orientations. Different orientations of perturbations may be provided by the perturbations extending in opposite directions with respect to the radius of the membrane. In a set of embodiments however all perturbations are oriented in the same direction relative to the radius.

The number of perturbations may vary on each wave. In a set of embodiments however the number of perturbations on each wave is the same. In such embodiments, the spacing of perturbations on larger diameter waves will be less dense compared with smaller diameter waves.

Adjusting various attributes of the waves and perturbations results in variations in the stiffness of the membrane. Different waves and perturbation arrangements will result in a membrane with different stresses and creeps. This may affect the sound attenuation provided by the membrane and the quality of the attenuated sound. Different wave and perturbation arrangements may also affect the behaviour of the membrane when the membrane is placed under different tensions by the adjustable member. A particular arrangement of waves and perturbations may therefore be selected to provide specific properties and performances of the membrane under particular tensions.

The device may comprise other features which help to provide increased control over the level of attenuation provided by the device. In a set of embodiments, the adjustable member comprises a compressible portion. The Applicant has appreciated that implementing an adjustable member with a compressible portion may be inventive in its own right without requiring the device to have a membrane comprising at least one corrugation. Therefore, when viewed from a second aspect the present invention provides a device, for insertion into an ear canal of a mammalian subject, comprising:
 a body, having a sound path extending therethrough;
 a tensioned membrane in the sound path; and
 an adjustable member comprising a compressible portion and arranged to bear against the adjustable membrane to adjust the tension of the membrane and thereby to alter an acoustic response of the sound path.

As with the first aspect of the invention, the arrangement of the membrane and the adjustable member allows for control of the sound passing through the sound path, e.g. the attenuation of the sound.

When the adjustable member contacts the membrane, the compressible portion of the adjustable member is compressed (and/or deformed), reducing the force exerted on the adjustable membrane by the adjustable member and resulting in a smaller increase in the tension of the membrane. Without the compressible portion referred to, the level of attenuation provided by the device would increase substantially when the adjustable member first contacts the membrane compared to the level of attenuation provided when the adjustable member is not in contact with the membrane and would increase rapidly thereafter, even with small movements. Therefore, as with the corrugation of the first aspect of the invention, the level of attenuation provided by the device may increase more smoothly and more gradually when the member contacts the membrane compared with a rigid member (i.e. with no compressible portion), to allow finer control over the attenuation provided by the device.

The compressible portion could be provided by any part of the adjustable member, but in a set of embodiments the compressible portion of the adjustable member contacts the surface of the membrane. This may aid the stability of the adjustable member.

The adjustable member may be arranged to have any suitable and desirable shape. There may be embodiments in which the compressible portion (which comprises part of the adjustable member) does not have the same shape as the remaining portion(s) of the adjustable member. For example, the compressible portion may be a cylinder with a smaller diameter than the remaining portion(s) of the adjustable member.

The compressible portion of the adjustable member may be shaped to be compressible (e.g. comprising a spring) and/or the compressible portion may be formed from a layer of inherently compressible material. Preferably, the compressible portion of the adjustable member is formed from an elastically compressible material. Whilst the Applicant has appreciated that the adjustable member could be formed from any suitable and desirable compressible material, in a set of embodiments, of either the first or the second aspect of the invention, the deformable portion is formed from thermoplastic elastomers or foam materials, e.g. polyurethane foam.

In a set of embodiments the adjustable member, or the rest of the adjustable member apart from the compressible portion, is formed from a rigid material. Whilst the Applicant has appreciated that the adjustable member could be formed from any suitable and desirable material, preferably the adjustable member is formed from a plastic. For example, the adjustable member is formed from a rigid plastic e.g. polycaprolactam (PA6), acrylonitrile butadiene styrene (ABS) or polyoxymethylene (POM).

In a set of embodiments, of either the first or the second aspect of the invention, the adjustable member comprises a central axis which is perpendicular to a plane or at least a central tangent plane of the membrane. In a set of embodiments, of either the first or second aspect of the invention, the adjustable member is rotationally symmetric about a central axis. This may help to ensure a uniform force is exerted on the membrane when the adjustable member is in contact with the membrane.

The adjustable member may be in contact with membrane throughout its travel However, in a set of embodiments of either the first or the second aspect of the invention, the adjustable member has a position wherein the adjustable member is not in contact with the membrane. In this position, the adjustable member does not exert a force on the membrane and therefore, the adjustable member does not alter the tension of the membrane from a base value.

It will be appreciated by the skilled person that when the adjustable member is in the non-contact position, the base level of attenuation provided by the device is lower than the level of attenuation provided by the device when the adjustable member is in contact with the membrane. This is because when the adjustable member is in contact with the membrane, the tension in the membrane is increased and therefore the attenuation of sounds by the membrane increases. The measures provided in accordance with the invention however mean that there is much less of a sharp change in performance between non-contact and contact as discussed previously than there would otherwise have been.

In a set of embodiments, in accordance with either the first or second aspect of the invention, the adjustable member has a plurality of positions wherein the adjustable member is in contact with the membrane. The plurality of positions of the adjustable member correspond to a plurality of magnitudes of force applied to the adjustable membrane, and therefore a plurality of tensions in the adjustable membrane. For example, as the adjustable member is moved further towards the membrane, the adjustable member exerts a greater force on the membrane and therefore the tension of the membrane is increased. The attenuation of the membrane is therefore greater and a higher level of attenuation is provided by the device.

As will be appreciated, it is desirable for the device to further comprise a mechanism for moving the adjustable member from one position to another. The position of the adjustable member may be adjusted in any suitable and desirable manner. In a set of embodiments, the device further comprises an adjustment arrangement for adjusting the position of the adjustable member. Preferably, the adjustment arrangement comprises an actuator for adjusting the position of the adjustable member.

In a set of embodiments of either the first or the second aspect of the invention, the actuator comprises an electric motor. The use of an electric motor may be advantageously mean that the device can automatically adjust the position of the adjustable member without requiring a physical input from a user. For example, the use of an electric motor may mean that the device can automatically adjust the attenuation of the sounds in loud environment, without requiring the user to take any action, thus protecting the user.

In another set of embodiments of either the first or the second aspect of the invention, the actuator comprises a user operable member. The user operable member may, for example, comprise a rotatable knob arranged to adjust the position of the adjustable member. A user operable member may advantageously simplify the device and reduce its cost. Through the use of a user operable member, it may be possible to achieve a device which does not comprise any electrical/electronic components, thereby potentially providing a device which does not require electrical power. Achieving a device which does not require electrical power may mean that the device is more frequently used as users do not have to concern themselves with ensuring that the device has enough battery power for operation. This may help to improve compliance with, for example, industry requirements to use hearing protection.

Preferably, the user operable member is connected to the adjustable member. In a set of embodiments, the user operate member is arranged to rotate the adjustable member relative to its central axis.

The device may further include an arrangement for converting rotational movement of the user operable member (relative to the central axis) to axial movement of the adjustable member. In a set of embodiments, the user operable member comprises a threaded portion and the body comprises corresponding threaded portion. In such a set of embodiments, the threaded portion of the user operable member is arranged to engage with a threaded portion of the body. Therefore, rotation of the user operable member causes a rotation of the adjustable member which results in linear movement of the adjustable member (i.e. to move the adjustable member towards or away from the membrane).

As will be appreciated by those skilled in the art, the pitch of the threaded portions may be chosen to allow for highly controlled movement of the adjustable member. Such control may be required to precisely control the tension of the membrane and therefore the level of attenuation provided by the device.

More generally, the adjustable member or user operable member may engage the body by means of one or more inclined surfaces so as to convert rotational movement of the user operable member and/or adjustable member to axial movement of the adjustable member.

In a set of embodiments, the adjustable member is arranged such that it can be held stable in a plurality of different positions. This may be achieved due to the presence of, for example, static friction. Alternatively, the device may comprise different means for holding the adjustable member stable. For example, the adjustable member and/or body may comprise a series of recesses and/or protrusions acting therebetween to hold the adjustable member stable when the recesses and protrusions are in engagement with one another. The position of the adjustable member could be thus adjustable continuously or incrementally.

In embodiments in which the actuator comprises a user operable member, different (e.g. rotational) positions of the user operable member may correspond to different stable positions of the adjustable member. These different (e.g. rotational) positions of the user operable member may be labelled to demonstrate to the user the level of attenuation (e.g. high, medium, low) provided by the device when the user operable member is in a particular rotational position.

Especially in embodiments in which there is a rotational movement of the adjustable member (relative to the central axis), a torsional drag forces may be generated between the base of the adjustable member and the membrane, which may inhibit smooth adjustments in the level of attenuation provided by the device. In a set of embodiments, of either the first or second aspects of the invention, the base of the adjustable member which contacts the membrane in use comprises a low friction coating or layer. In a set of embodiments, the coating or layer comprises polytetrafluoroethylene (PTFE). The coating or layer may help to reduce the aforementioned torsional drag forces between the adjustable member and the membrane. In embodiments wherein the adjustable member comprises a compressible portion, the compressible portion may comprise the friction coating or layer, or a separate low fiction coating or layer could be applied to the surface thereof which contacts the membrane. Alternatively, the adjustable member may be formed from a material with self-lubricating properties e.g. polyoxymethylene (POM) and/or the adjustable member may include friction reducing additives e.g. polytetrafluoroethylene (PTFE).

The membrane may be in the form of a relatively thin sheet of material on, or in, the device. Preferably thickness of the film is in the range of 1 to 20 μm. In an exemplary set of embodiments, the membrane is made from a plastic film e.g. polyethylene terephthalate (PET). Whilst the corrugation can be provided in any suitable and desired way, in a set of embodiments the corrugation is stamped into the membrane.

The membrane may be integral to the body of the device. For example, the membrane may be integrally moulded with the body, or the body may be milled in order to form the membrane. However, the Applicant has recognised that integrally providing the membrane with the body may be complicated to manufacture. In a set of embodiments in accordance with the first or second aspect of the invention, the adjustable membrane is a separate component attached to the body. In a further set of such embodiments, the body defines a rim to which the adjustable membrane is attached. This may allow for a simpler manufacture of the body. Additionally, it may allow the body and the adjustable membrane to be manufactured from different materials which may be desirable in order to provide a membrane with the required mechanical properties. For example, the adjustable membrane may be made from a plastic film, e.g. polyethylene terephthalate (PET) whilst the body may be made from e.g., polycaprolactam (PA6) (e.g. the body may be formed from the same material as the adjustable member and the membrane formed from a different material).

In a set of embodiments, according to either the first or second aspect of the invention, the adjustable membrane is circular. This may allow for a more uniform tensioning of the membrane, compared to membranes having alternative shapes, e.g. square shaped membranes. The diameter of the membrane may be in the range 4 mm to 20 mm (i.e. corresponding to radii in the range of 2 mm to 10 mm). In embodiments in which the adjustable membrane is circular and the body defines a rim to which the membrane is attached, it is preferable that the rim is also circular.

Preferably the membrane is essentially planar (e.g. in the plane perpendicular to the central axis of the adjustable member) and smooth, apart from any corrugations.

When the adjustable member is applying the least amount of force—which may be zero if the adjustable member has a position where it is not in contact with the membrane, the membrane can be considered to be under a base tension. The base tension may be provided solely by the attachment of the membrane to the rim of the body. The base tension may also be described as the minimum tension of the membrane. When the adjustable member is moved into or further into contact with the membrane, the tension in the membrane is increased above the base tension. The base tension of the membrane may result in a relatively low level of attenuation of sounds so that, for example, a user can still communicate orally with fellow workers.

In a set of embodiments, according to either the first or second aspect of the invention, the adjustable member is arranged to contact the membrane in the geometric centre of the membrane. In some embodiments, the geometric centre of the membrane is flat. In another set of embodiments, the centre of the membrane is domed. For example, in embodiments wherein the membrane comprises a corrugation (e.g. a wave), the dome should preferably be smaller than the corrugation. The dome shape may help to control the contact between the adjustable member and the membrane when the member first comes into contact with the membrane.

The membrane may be described as comprising part of an adjustable acousto-mechanical portion of the device. In a set of embodiments, the device comprises a further adjustable acousto-mechanical portion comprising an adjustable channel forming at least part of the sound path (i.e. another part of the sound path to the membrane), and the device further comprises an adjustment arrangement for adjusting the further acousto-mechanical portion. The further acousto-mechanical portion may be arranged to vary the level and/or vary different qualities of the attenuation provided by the device.

In a set of embodiments, in accordance with either the first or the second aspects of the invention, the device comprises a first adjustable acousto-mechanical portion comprising an adjustable channel forming at least part of the sound path and a second adjustable acousto-mechanical portion arranged acoustically in series with the first acousto-mechanical portion comprising the membrane as described hereinabove, and an adjustment arrangement comprising said adjustable member for simultaneously adjusting the first and the second acousto-mechanical portions to alter the acoustic response of the at least one sound path.

In this set of embodiments, the tensioned membrane constitutes an adjustable member forming part of a second adjustable acousto-mechanical portion. The Applicant has recognised that with the arrangement of the adjustable channel and the adjustable membrane, it is possible to achieve an acoustic response of the sound path which does not significantly reduce the quality of the sound passing through the sound path whilst maintaining the ability to control the sound, e.g. by attenuating the sound. This is because it allows the changes in the channel and membrane as they are adjusted to complement one another to maintain a favourable acoustic response.

As will be understood by those skilled in the art, the acoustic response of the sound path should be understood to be how the sound path affects the sound which passes through it. The acoustic response of the sound path may change the frequency, amplitude and/or phase of the sound passing through it and thus ultimately change the sound heard by a user of the device.

The adjustment arrangement may comprise any suitable arrangement for adjusting the first adjustable acousto-mechanical portion and the second adjustable acousto-mechanical portion. In a set of embodiments the adjustment arrangement, comprises a first actuator for adjusting the first adjustable acousto-mechanical portion and a second actuator for adjusting the adjustable member (i.e. that which is arranged to bear against the membrane). The first and second actuators may, for example, be connected to a single controller capable of simultaneously controlling each of the first and second adjustable acousto-mechanical portions. Such an arrangement may be particularly advantageous when the first and second adjustable acousto-mechanical portions require adjustment by differing amounts, e.g. due to the need to achieve a particular acoustic response. Having separate actuators for each adjustable acousto-mechanical portion may make it possible to adjust one of the portions through a greater proportion of its physical range of movement than the other if required in a particular instance to achieve a desired response.

In an alternative set of embodiments in accordance with either aspect of the invention, the adjustment arrangement comprises a common actuator arranged to adjust both the first and second acousto-mechanical portions simultaneously. The Applicant has found that the use of such a common actuator may be advantageous, for example in embodiments wherein the device is electrically powered as it may reduce the amount of power required to adjust the first and second adjustable acousto-mechanical portions. It may also simplify the construction of the device. Of course by suitable design of such an actuator, e.g. to include one or more levers or members of differing stiffness, different amounts of movement may be imparted to the respective acousto-mechanical portions for a given input movement. The common actuator could act on, or be provided by, the above-mentioned adjustable member.

In a set of embodiments in accordance with either aspects of the invention, the or each actuator comprises an electric motor. However, in another set of embodiments, the or each actuator comprises a user operable member arranged to operate at least part of the adjustment arrangement.

The first adjustable acousto-mechanical portion comprising the adjustable channel may be adjusted in any appropriate manner in order to achieve the desired acoustic response. In a set of embodiments the adjustment arrangement is configured to adjust a length of the adjustable channel. The Applicant has recognised that adjusting the length of the adjustable channel may in general alter the effect of the channel. Additionally or alternatively, the adjustment arrangement is configured to adjust a width of the adjustable channel. The Applicant has found that adjusting the width of the adjustable channel may serve to adjust the specific acoustic properties of the sound path. For example, decreasing the width of the channel will typically increase the effective acoustic mass and the acoustic loss of the channel and vice versa. Conversely decreasing the length of the channel will typically decrease the effective acoustic mass and the acoustic loss of the channel and vice versa. In other words the acoustic mass and loss typically have a positive relationship with the length of the channel and a negative relationship with the width of the channel. The terms acoustic mass and acoustic loss are well known to those skilled in the art but will be further explained later.

As will be appreciated, the length and width of the adjustable channel may be adjusted independently of one another, or simultaneously together. In a potentially overlapping set of embodiments, the adjustment arrangement is configured to adjust a shape of the adjustable channel.

The adjustable channel may be defined by any suitable structure within the device. For example, the channel may simply comprise a cylindrical channel extending through the body of the device. Adjustment of such a channel may, for example, comprise constricting and expanding the body so as to decrease/increase the size of the channel. In a set of embodiments in accordance with either the first or second aspect of the invention, however, the channel is defined by a space between a wall of a cavity within the body and a piston arranged in the cavity, wherein adjustment of the channel is achieved by moving the piston relative to the cavity.

The piston may act on, or preferably be provided by, the adjustable member of either of the first or second aspects of the invention.

The cross-section of the channel will depend on the shape of the wall of the cavity and the outer profile of the piston. The piston may have a complementary sectional shape to the wall of the cavity, e.g. if the wall has a circular sectional shape, the piston may have a circular sectional shape. In such an example, the channel defined between the wall and piston would effectively be an elongate annular channel. The Applicant has recognised that the arrangement of a piston in the cavity provides for a relative simple means to adjust the length and/or cross-sectional area and/or shape of the channel.

The piston may be arranged in the device in any suitable manner such that it can be moved relative to the cavity. For example, the piston may be a part of, or attached to, a linear actuator capable of moving the piston into, and out of, the cavity. In a set of embodiments, the piston is arranged to move axially within the cavity and the device comprises at least one resilient member arranged to bias the piston into or out of the cavity, wherein the adjustment arrangement comprises an actuation member arranged to drive the piston against the resilient bias axially out of or into the cavity respectively. The actuation member may be driven by an electric motor or a user operable member. The Applicant has recognised that the provision of a resilient member arranged in the manner according to the above set of embodiments means that the actuation member needs only to be able to drive movement in one axial direction as the resilient member is arranged to drive movement of the piston in the other axial direction. This may simplify the manufacture and construction of the device. In a set of embodiments, the actuation member is arranged to rotate relative to the piston, and the device further comprises an arrangement for converting rotational movement of the actuation member into axial movement of the piston. The resilient member may be integrally provided with the piston. In a further set of embodiments, a plurality of resilient members is provided. In another set of embodiments, the at least one resilient member is in the form of a resilient arm extending between the piston and the body. Of course, in addition or alternatively, the piston may be arranged to move in other directions other than just axially. For example, the piston may be moved at a non-zero angle to the axis, be translated from side-to-side within the cavity or even twisted, in order to adjust the channel so as to achieve a desired acoustic response.

The Applicant has recognised that in order to appropriately control the acoustic response of the sound path, it may be necessary to adjust the length and cross-section of the adjustable channel simultaneously. In a further set of embodiments in accordance with either aspect of the invention, the cavity and the piston each have a frusto-conical shape such that the adjustable channel has the form of a frusto-conical shell. The Applicant has recognised that in such an arrangement axial movement of the piston within the cavity may simultaneously adjust both the length of the channel and the width. It may also mean that a relatively large axial movement can be converted into a relatively small change in width. This may help to simplify the manufacture and construction of the device and to provide fine control over the width. The piston and cavity are preferably shaped so that the channel remains of uniform shape throughout the travel of the piston but this is not essential.

Some preferred embodiments of the present invention will now be described, by way of example only, and with reference to the accompanying drawings, in which:

FIG. 1b shows an alternate isometric view of the device seen in FIG. 1a;

FIG. 2a shows an exploded view of parts of the device seen in FIG. 1a;

FIG. 2b shows an isolated isometric view of the body of the device seen in FIG. 1a;

FIG. 3 shows the piston, user operable member and the membrane of the device seen in FIG. 1a;

FIG. 4 shows an isolated isometric view of the adjustable member and user operable member of the device seen in FIG. 1a;

Figure 1A:
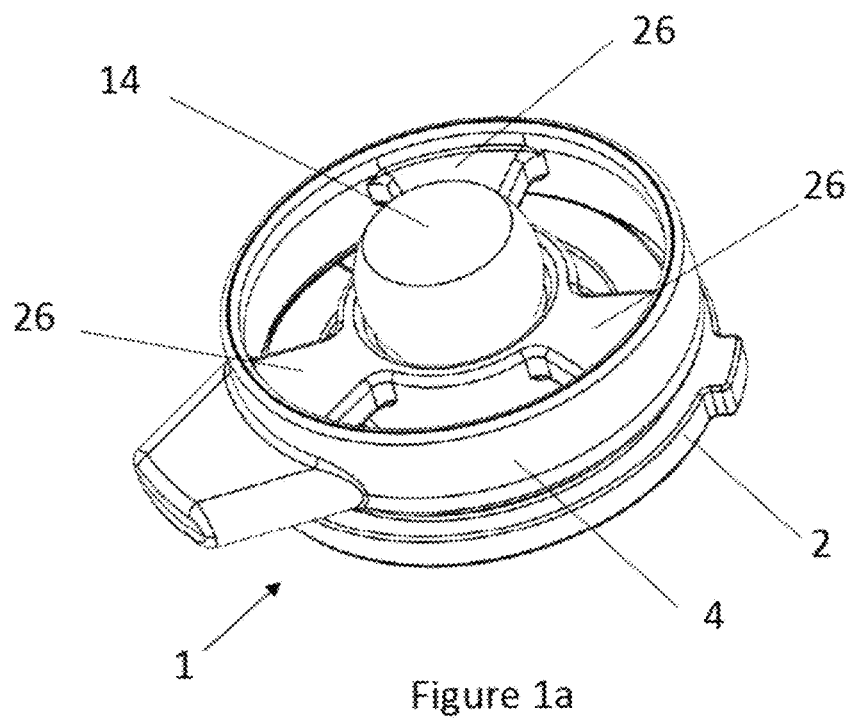
FIG. 1a shows an isometric view of part of a hearing protection a device in accordance with an embodiment of the present invention.

FIG. 1a shows an isometric view of part of a hearing protection device in accordance with an embodiment of the present invention. The device is designed for insertion into a human inner ear canal and in practice would be fitted with a flexible 'cone' or a bespoke moulded insert to facilitate this. As can be seen in FIG. 1a, the device 1 includes a body 2 upon which a user operable member in the form of a handle member 4 is located.

The device 1 further comprises a resiliently compressible member 14, which is located upon the handle member 4. The compressible member 14 is arranged to apply a force to the various components of the device 1 to maintain the handle member 4 and the body 2 in position with respect to each other e.g. when the handle member 4 is rotated. The compressible member 14 can be compressed by varying degrees.

Figure 1B:
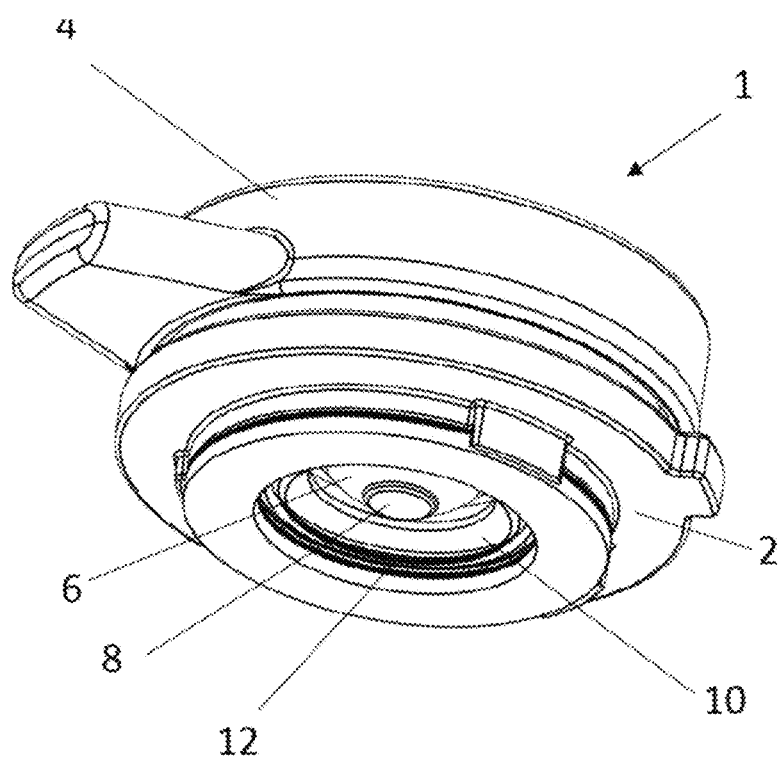

FIG. 1b shows an isometric view of the underside of the device shown in FIG. 1a. Arranged towards the base of the device 1 is a circular membrane 10. Whilst the membrane shown in FIG. 1b is transparent, this is not essential and the membrane could be opaque. The membrane is attached to the body 2 of the device, in particular bonded to a circular rim 22 (as can be seen in more clearly in FIG. 2a) formed within the body 2 of the device 1.

As can be seen from FIG. 1b, the handle member 4 is integrally formed with a tapering adjustable member in the form of a piston 6 which comprises a compressible portion 8 at its distal end in the form of a disc of compressible material such as a closed cell foam or thermoplastic elastomer. As will be explained later, the compressible portion 8 is arranged to contact the membrane 10 to increase the tension of the membrane 10. The piston 6 is attached to the handle member 4 by means of three spokes 26 which extended from the circumference of the handle member 4 to the piston 6 so that movement of the handle member 4 results in the movement (e.g. adjustments) of the piston 6. The movement of the piston 6 changes the degree of compression of the compressible member 14.

The handle member 4 can be rotated with respect to the body 2 of the device 1. In particular, the handle member 4 may be moved by a user to a variety of different rotation positions with respect to the body 2 of the device. When the handle member 4 is rotated, the piston 6 also rotates. The conversion of rotational movements of the handle member 4 to axial (linear) movement of the piston 6 will be discussed in more detail in relation to FIGS. 5-10. As will also be discussed in further detail in relation to FIGS. 5-10, different rotational positions of the handle member 4 correspond to different attenuations provided by the device 1.

Figure 3:
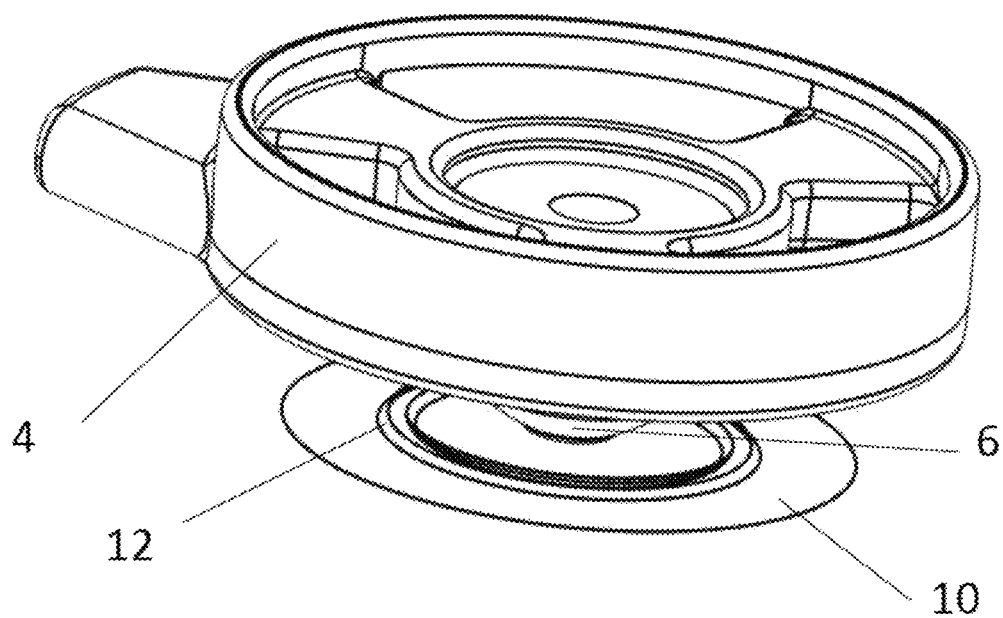

The membrane 10 further comprises a corrugation 12. The corrugation 12 can be seen more clearly in FIG. 3 which shows an isometric view of the isolated handle member 4 and membrane 10 of the device shown in FIG. 1. The corrugation 12 is a circular ridge centred on the geometric centre of the membrane 10 which extends above the plane of the membrane 10. This arrangement of the corrugation 12 means that the compressible portion 8 does not come into contact with the corrugation 12 (e.g. the compressible portion 8 contacts the membrane 10 in the geometric centre of the membrane 10). The cross-section of the ridge resembles a bell curve, which can be seen more clearly in the cross-sectional views seen in FIG. 5-7.

Figure 2A:
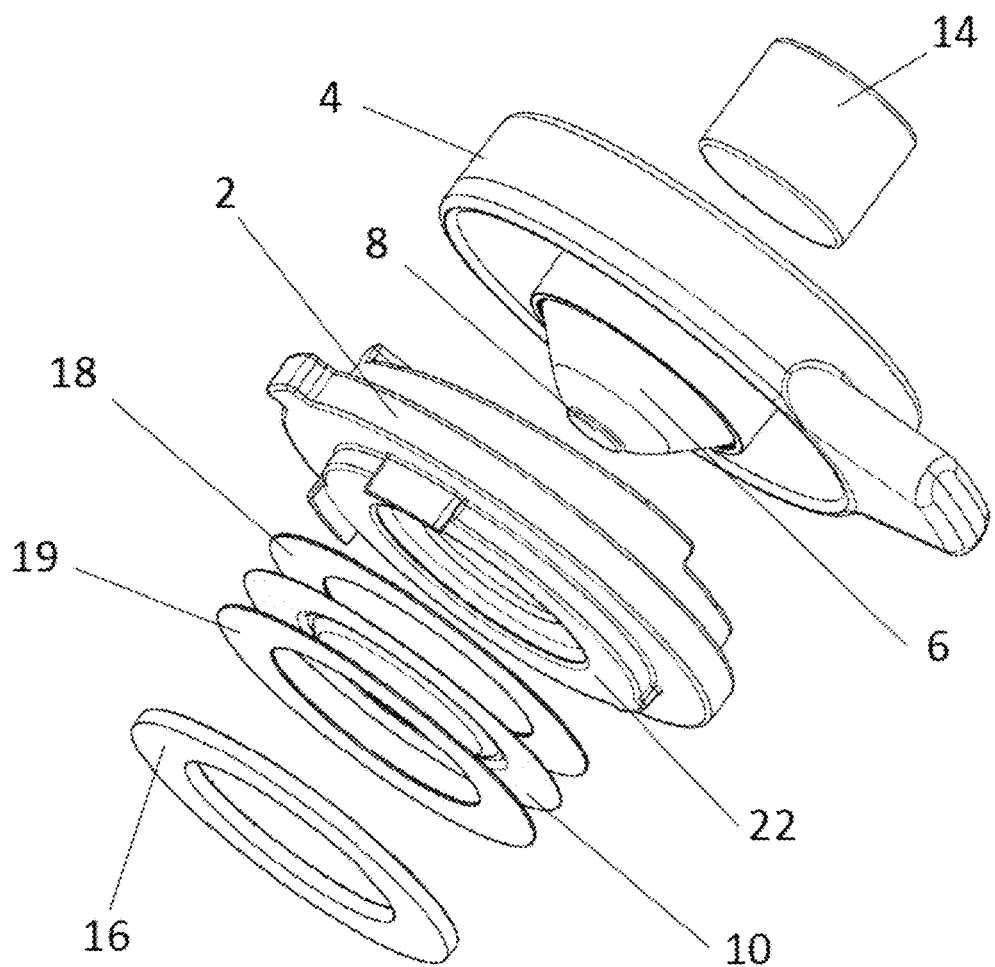

FIG. 2a shows an exploded view of the device seen in FIG. 1. Starting from the top, FIG. 2a shows the compressible member 14 and the handle member 4. The handle member 4 is essentially circular with a protruding grip portion. As previously discussed, the handle member 4 is integrally formed with a piston 6. The piston 6 extends below the handle member 4 and is concentric with it. FIG. 2a also shows the tensioned membrane 10 which comprises the aforementioned corrugation 12.

In FIG. 2a, the rim 22 which forms part of the body 2 of the device 1 can be seen. The membrane 10 is secured in position on the rim 22 by a stabilising ring 16 and two adhesive tape rings 18, 19. The stabilising ring 16 and tapes 18, 19 have the same shape as the rim 22. When the device is constructed, the first tape 18 is positioned between the rim 22 and the membrane 10. The second tape 19 is positioned between the membrane 10 and the stabilising ring 16. The stabilising ring 16 holds the membrane 10 in position during formation of the corrugation 12 in the production process.

Figure 2B:
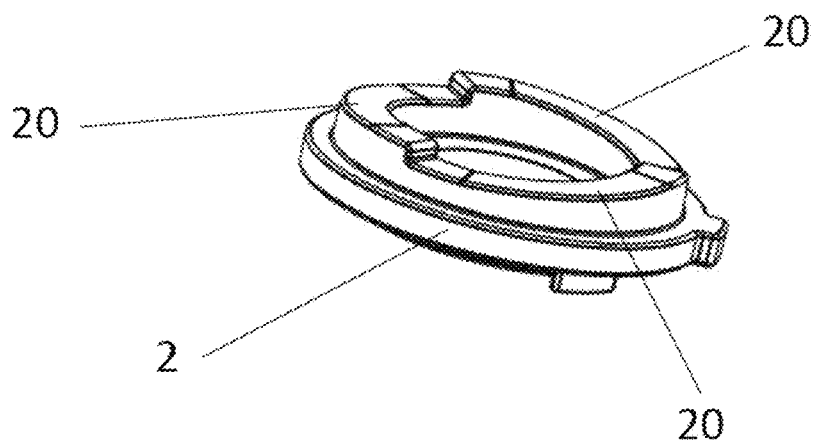
Figure 4:
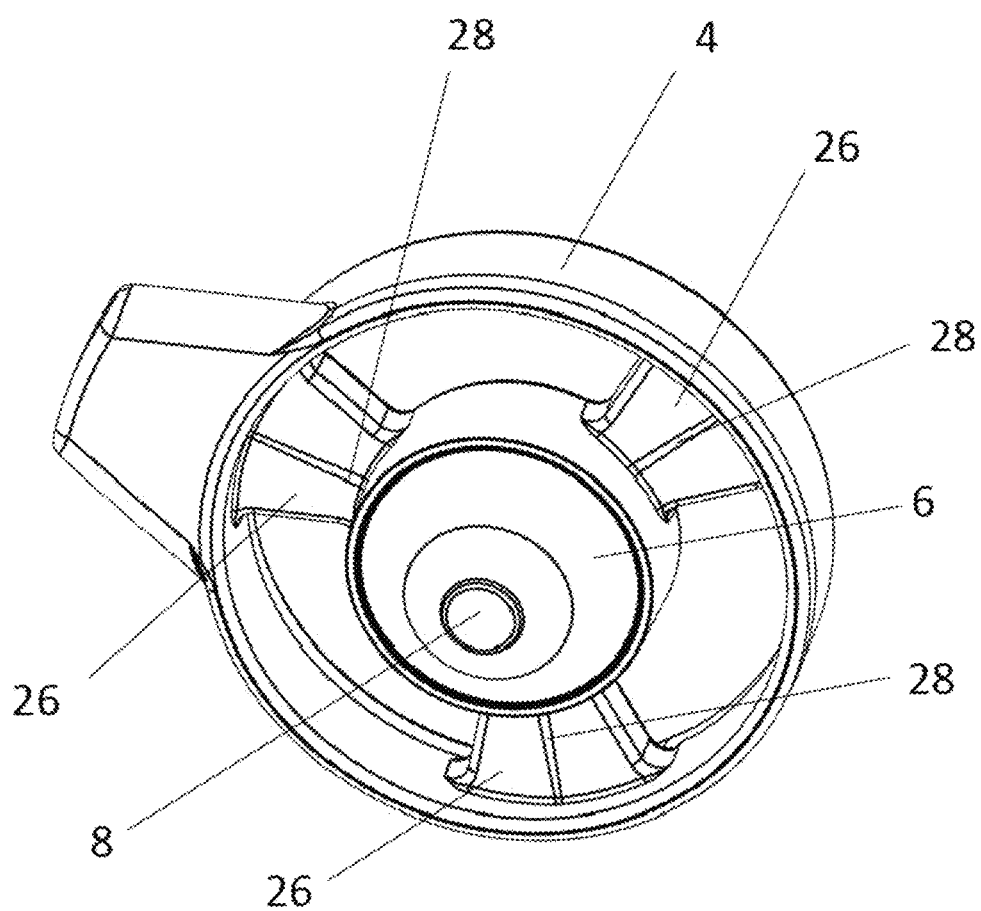

In the embodiment of the device shown in FIG. 2b, the body 2 includes three inclined cam surfaces 20, located on the uppermost surface of the body 2. FIG. 4 shows an isometric view of the underside of the handle member 4 and piston 6 in isolation. In this isolated view, the underside of each of the spokes 26 of the handle member 4 can be seen to comprise a ridge 28 on its underside. When the device is assembled (e.g. as seen in FIGS. 1a and 1b), each of the ridges 28 contacts a corresponding inclined cam surface 20 of the body 2 of the device 1.

Operation of the device will now be described with reference to FIGS. 5 to 10.

Figure 5:
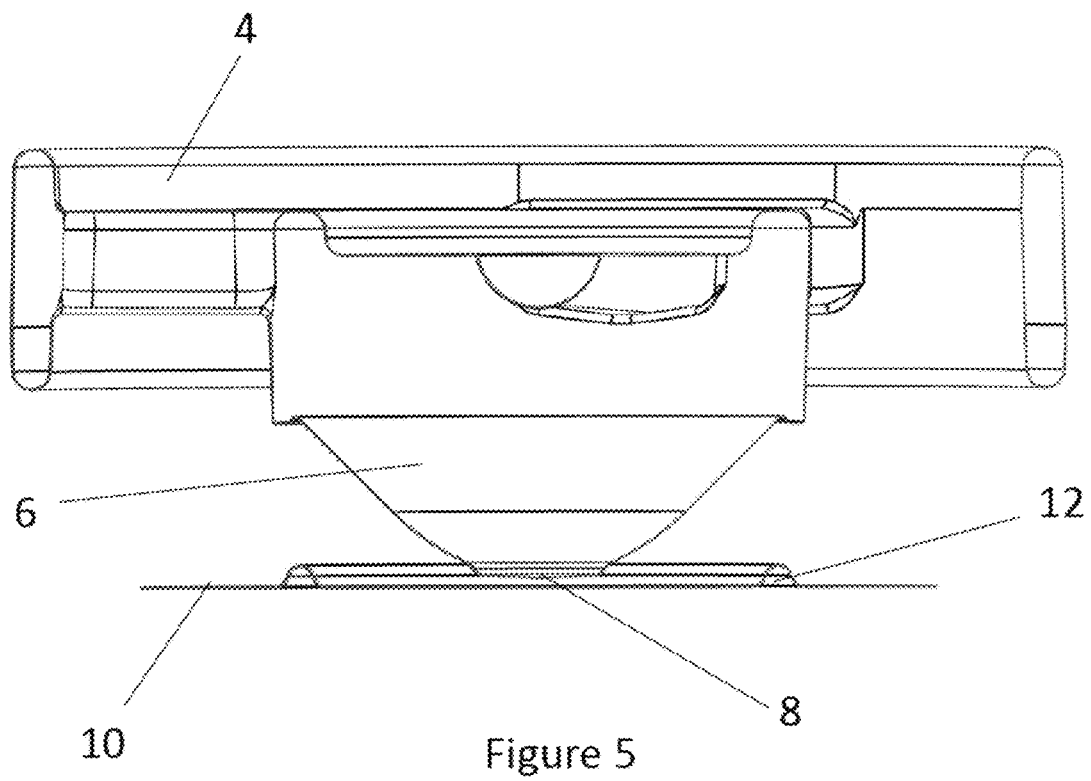
FIG. 5 shows a cross-sectional view through certain components of the device in a first configuration.
Figure 6:
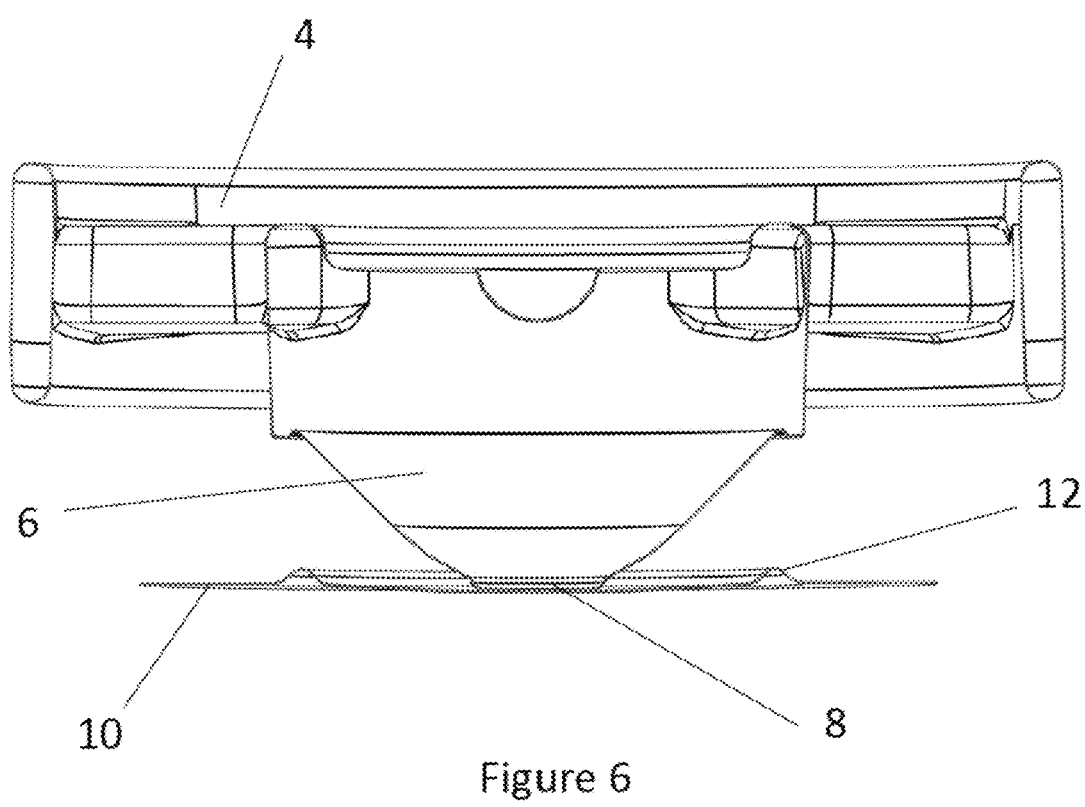
FIG. 6 shows a cross-sectional view through certain components of the device in a second configuration.
Figure 7:
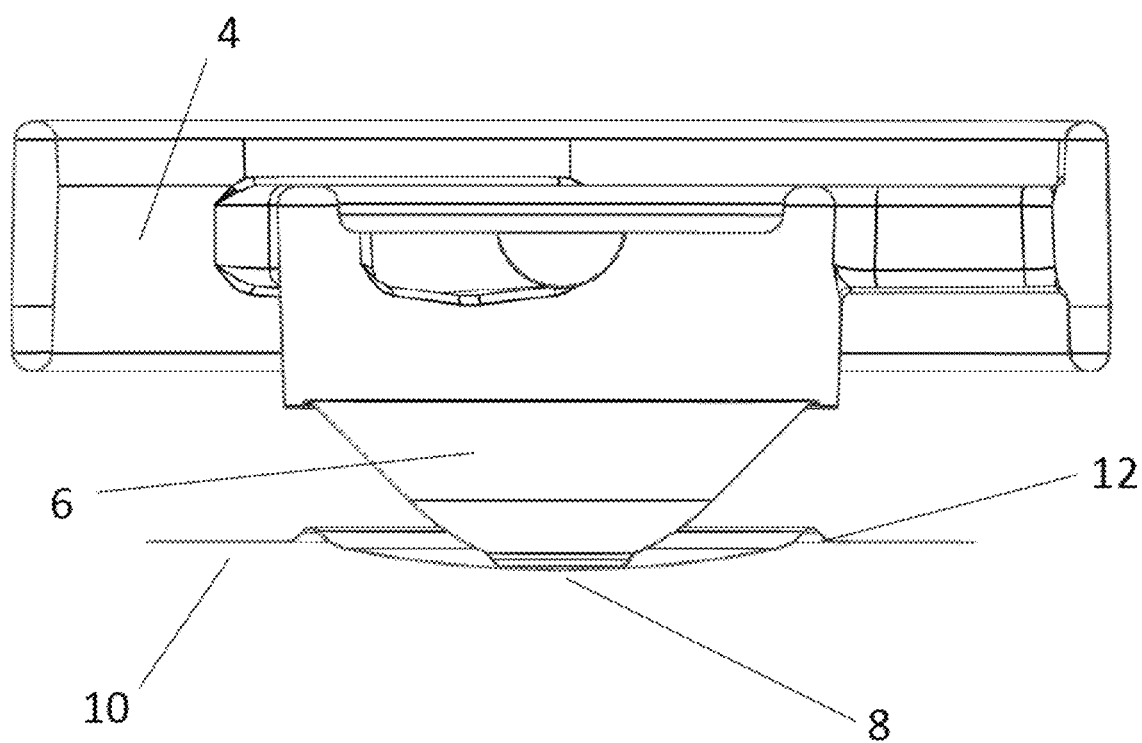
FIG. 7 shows a cross-sectional view through certain components of the device in a third configuration.

FIGS. 5-7 are illustrations demonstrating how the position of the piston 6 can be used to adjust the tension of the membrane 10. For clarity, these illustrations show a cross-section through the handle member 4, the piston 6 and the membrane 10 in isolation from the other components of the device 1.

Figure 8:
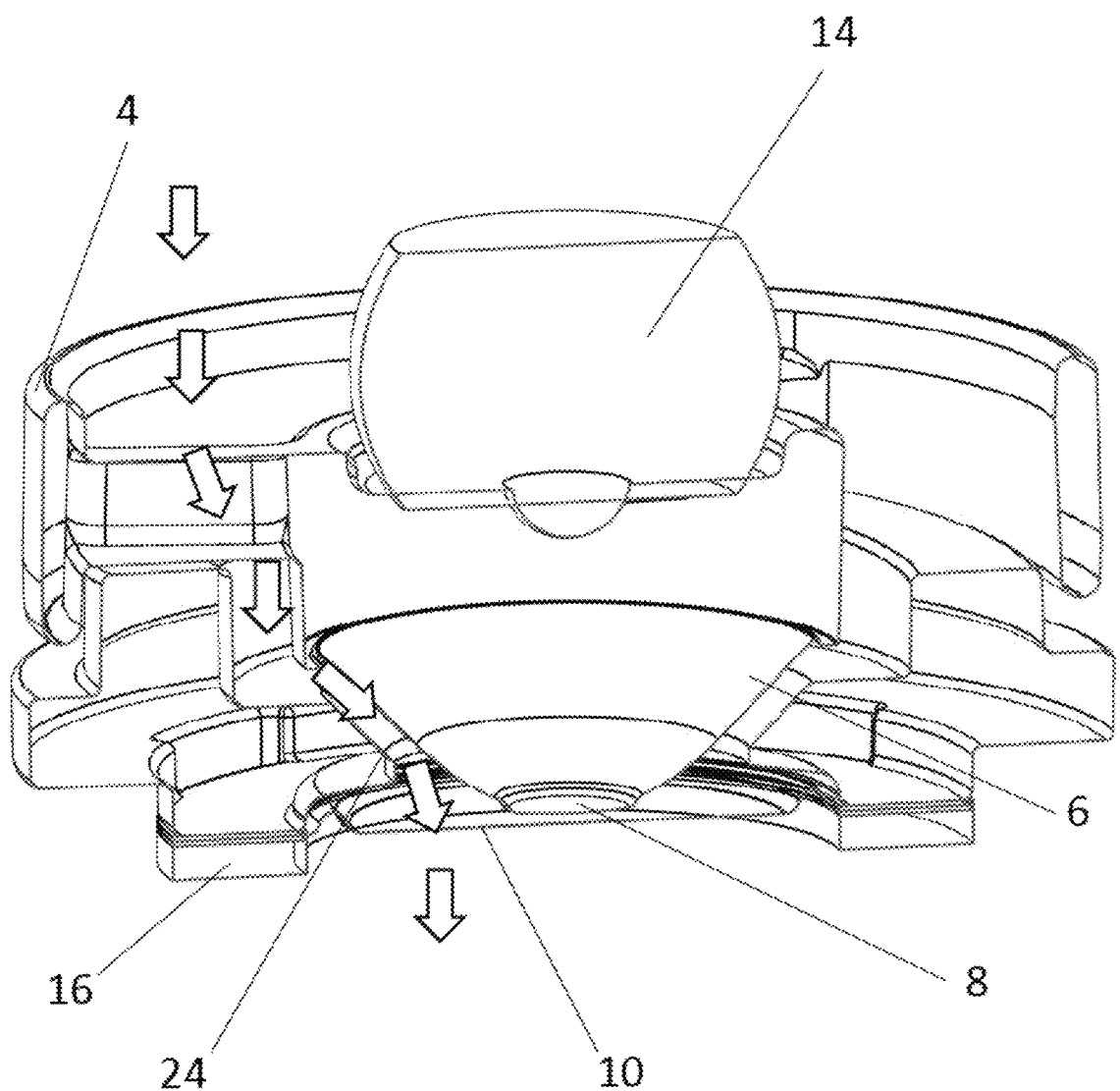
FIG. 8 shows another cross-sectional view through the device seen in FIG. 1a in the first configuration.
Figure 9:
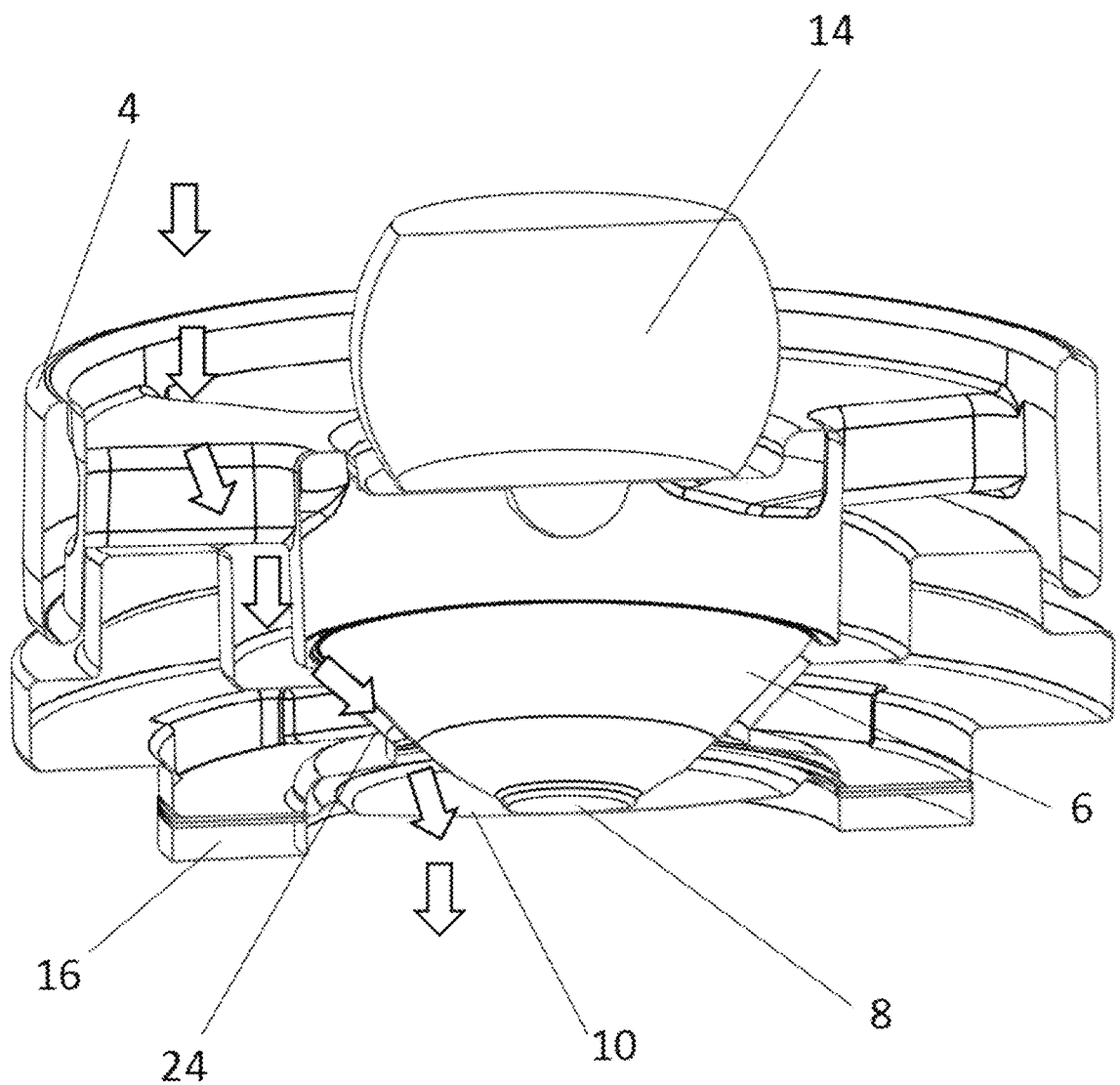
FIG. 9 shows another cross-sectional view through the device seen in FIG. 1a in the second configuration.
Figure 10:
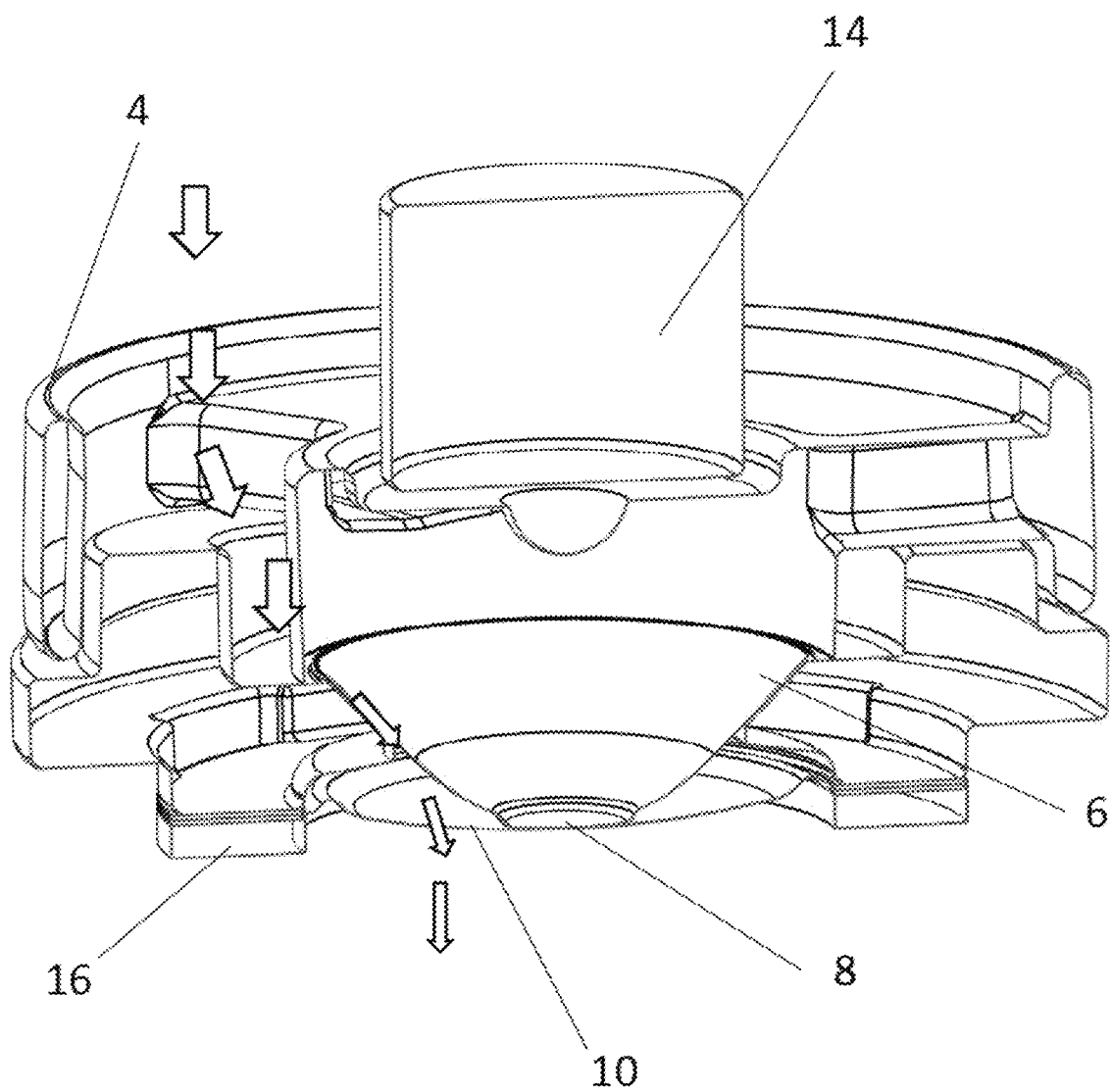
FIG. 10 shows another cross-sectional view through the device seen in FIG. 1a in the third configuration.

FIGS. 8-10 are illustrations demonstrating how the position of the piston 6 can also be used to adjust the dimensions of a channel 24. In the embodiments shown in the FIGS. 5-10, the piston 6 simultaneously adjusts the dimensions of the channel 24 and the tension of the membrane 10.

When the handle member is in the first position shown in FIGS. 5 and 8, each ridge 28 contacts the corresponding inclined cam surface 20 at its highest point. As a result of this, the piston 6 is not in contact with the membrane 10. In this position, the piston 6 applies zero force to the membrane 10. The tension in the membrane 10 is therefore the base tension (i.e. the minimum tension in the membrane). This base tension is provided by the attachment of the membrane 10 to the rim 22 of the body 2. The compressible member 14 is in a compressed state, which biases the movement of the piston 6 axially downwards towards the membrane 10.

As shown in FIG. 8, when the handle member 4 is in the first position, a channel 24 is formed between the wall 30 of the cavity formed by the body 2 of the device 1 and the piston 6. The arrows illustrate how sound propagates through the device along a sound path which includes the channel 24.

The handle member 4 may then be rotated by the user to a second position, as shown in FIGS. 6 and 9. In the second position of the handle member 4, each ridge 28 contacts the corresponding inclined cam surface 20 at the middle point of the inclined cam surface 20. When the handle member is rotated from the first position to the second position, each ridge moves down the corresponding inclined cam surface 20. The whole of the handle member 4 moves axially downwards towards the body 2 of the device 1 and therefore the piston 6 is moved axially downwards towards the membrane 10. Together, the inclined cam surfaces 20 and ridges 28 on the spokes 26 convert the rotational movement of the handle member 4 to axial movement of the piston 6.

In the second position shown in FIG. 6, the piston 6 is in a position in which the piston 6 just contacts the surface of the membrane 10. In the absence of a corrugation, when the piston 6 contacts the membrane 10, the primary vibration mode of the membrane 10 is disabled and the centre of the membrane 10 can be considered to be held stationary. Therefore, only higher order harmonic vibration modes of the membrane 10 are enabled, resulting in an abrupt increase in the attenuation. Including the corrugation 12 in the membrane reduces this effect. Therefore, the level of attenuation is more smoothly increased when the piston just contacts such a membrane 10 which includes a corrugation 12.

As the piston 6 comprises a compressible portion 8, some of the force which would have otherwise been exerted on the membrane 10 (e.g. compared with a rigid piston with no compressible portion) acts to compress the compressible portion 8. This results in a smaller force being exerted on the membrane 10 by the piston 6 and therefore a smaller increase in tension of the membrane 10. The level of attenuation is therefore increased more gradually when the piston 6 is moved to just contact the surface of the membrane 10 (compared with a rigid member).

In the second position as shown in FIG. 9, the piston 6 is positioned so as to decrease the dimensions (e.g. the width and/or the length) of the channel 24 compared with the first position. As will be described later, decreasing the width of the channel 24 increases the effective acoustic mass and the acoustic loss of the channel 24. Decreasing the length of the channel 24 decreases the effective acoustic mass and the acoustic loss of the channel 24. This, together with the altered tension of the membrane 10, changes the overall response of the device 1.

The handle member 4 may be further rotated by the user to a third position, as shown in FIGS. 7 and 10. In the third position of the handle member 4, each ridge 28 contacts the corresponding inclined cam surface 20 at the lowest point. This corresponds to limit of rotational movement of the handle member 4 (in this direction) and therefore the limit of axial movement of the piston (towards the membrane).

In the third position shown in FIG. 7, the piston is in contact with the surface of the membrane, and exerts a larger (e.g. a maximum) force on the membrane (e.g. than was exerted when the handle member 4 was in a second position and the piston 6 just contacted the surface of the membrane 10). The force exerted by the piston 6 also causes a more pronounced deformation of the rest of the membrane 10. As can be seen in FIG. 7, in this position the membrane 10 is deformed from essentially planar to concave or frusto-conical as a result of the force exerted on the membrane 10 by the piston 6. In this configuration, the tension of the membrane 10 is increased further above the base tension (e.g. the tension is increased to its maximum). This results in the attenuation provided by the device 1 being greater (i.e. than the attenuation provided by the device 1 when the handle member is in the first or second positions shown in FIGS. 5 and 6 respectively).

In the third position shown in FIG. 10, the piston 6 contacts the walls of the cavity in body 2 of the device 1. Therefore, there is a minimal channel width (e.g. no channel) between the walls of the cavity of the body and the piston 6. In this arrangement, the minimal channel width together with the high tension of the membrane, both results in the device providing its maximum attenuation. The compressible member 14 is decompressed.

In embodiments in which the attenuation provided by the device is at a minimum, when the handle member is in the first position, the channel 24 may be described as 'open' and the device 1 may be described as being in an 'open' configuration. In embodiments in which the attenuation provided by the device is at a maximum when the handle member is in the third position, the channel 24 may be described as 'closed' and the device 1 may be described as being in a 'closed' configuration.

Of course, as will be appreciated by those skilled in the art, the handle member 4 may be moved to any intermediate position between the first, second and third positions seen in FIGS. 5-7 and 8-10, in order to achieve a desired acoustic response of the sound path.

Figure 11A:
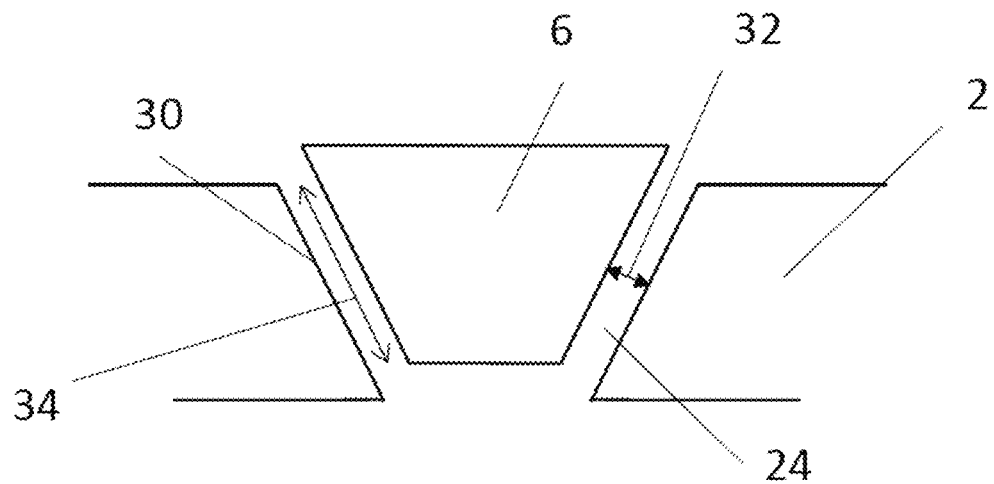
FIGS. 11a and 11b are illustrations demonstrating how the dimensions of a channel can be adjusted using an adjustable member.
Figure 11B:
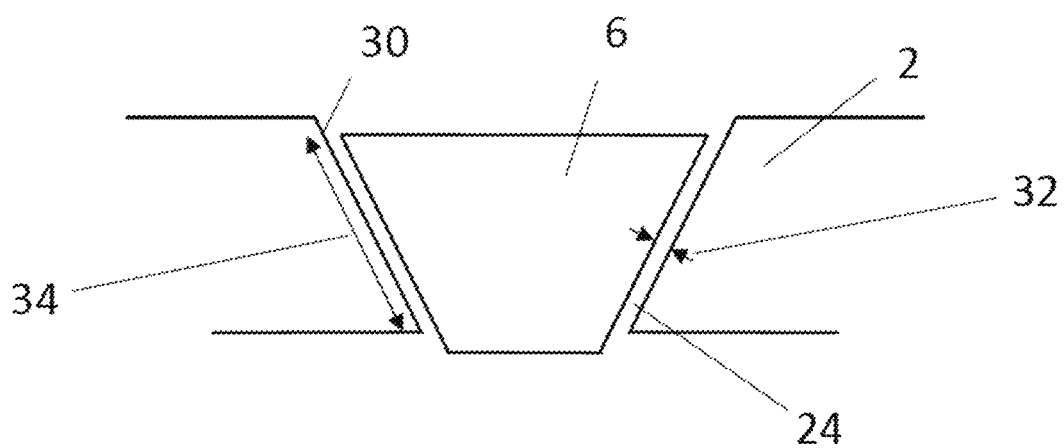

FIGS. 11a-11b are illustrations demonstrating how the position of a piston, or in the device shown in FIG. 1, the piston 6 in the cavity of the body 2 can be used to adjust the channel 24. When the piston is in the position seen in FIG. 11a, the channel 24 has a length shown by arrow 34 and a width shown by arrow 32. As demonstrated by FIG. 11b, when the piston 4 is moved axially into the cavity, the length of the channel shown by arrow 34 and the width of the channel shown by arrow 32 are both changed. Accordingly, changing the axial position of the piston 4 relative to the cavity of the body 2 will adjust the channel 24. As will be appreciated by those skilled in the art, adjusting the dimensions of the channel 24 will serve to alter the acoustic response of the channel 24 and thus alter the acoustic response of the sound path. More specifically the width, d, of the channel is related to the acoustic loss and the acoustic mass of the channel. Under the electrical circuit analogy for analysis of acoustic systems which will be familiar to those skilled in the art, the acoustic loss is equivalent to a resistance R and has an inverse cube relationship to the channel width as shown below:

$$R = k_1 \frac{1}{d^3} \quad \text{(Eq 1)}.$$

where $k_1$ is a constant representing parameters assumed to remain constant such as air density and dimensions.

Under the same electrical analogy, the acoustic mass is equivalent to an inductance, L and has an inverse relationship to the channel width, d:

$$L = k_2 \frac{1}{d} \quad \text{(Eq 2)}.$$

where $k_2$ is a constant representing parameters assumed to remain constant such as air density and dimensions.

The resistance R and the inductance L are both directly proportional to the length of the channel.

Following the aforementioned electrical analogy, when a membrane is tensioned the acoustic capacitance will decrease. As this capacitance is in series with the acoustic capacity of the ear canal, but also the resistance and inductance of the transmission path through the channel, this will cause the attenuation to increase, but will also change the frequency response. In accordance with the invention the changes in acoustic resistance, inductance and capacitance can be tuned so that the change in frequency response matches the natural frequency response of the human ear so that the frequency spectrum perceived by a user is essentially flat.

In the device 1, shown in the Figures when the user rotates the handle member 4, the dimension of the channel 24 and the tension of the membrane 10 are simultaneously adjusted. The simultaneous changes in the dimensions of the channel 24 and the tension of the membrane 10 complement one another, and therefore it is possible to achieve an acoustic response of the sound path which does not significantly reduce the quality of the sound passing through the sound path whilst maintaining the ability to control the sound e.g. by attenuating the sound.

Figure 12:
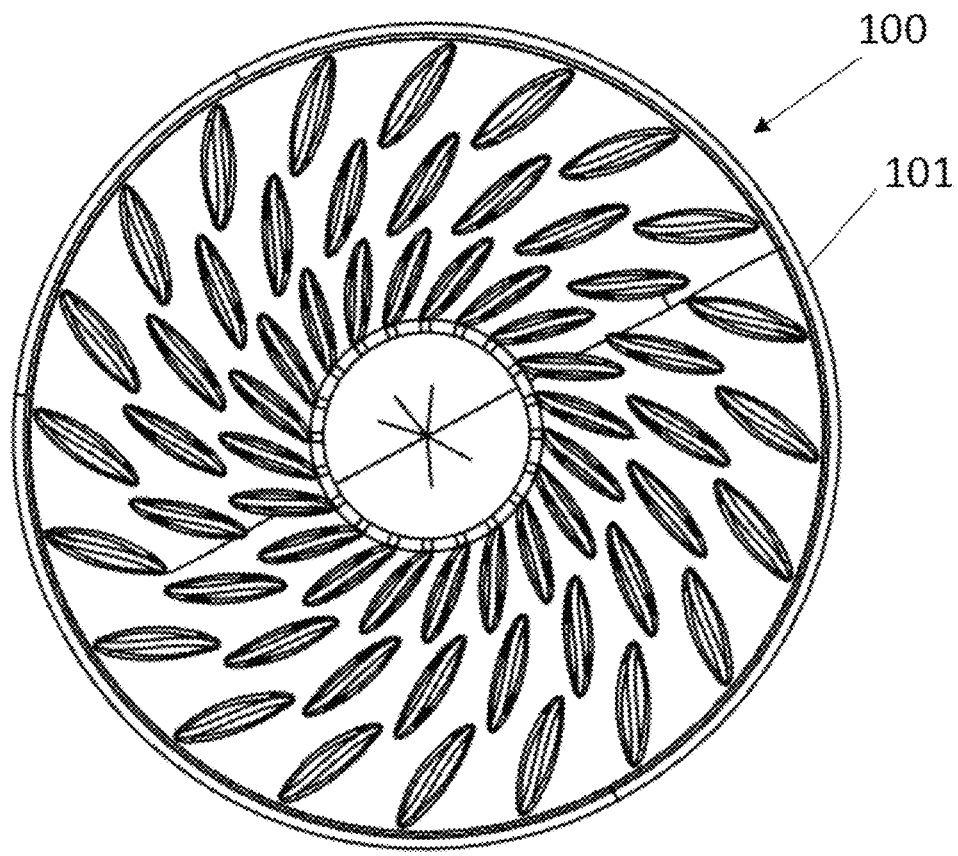
FIG. 12 shows a plan view of a membrane in accordance with another embodiment of the present invention.
Figure 13:
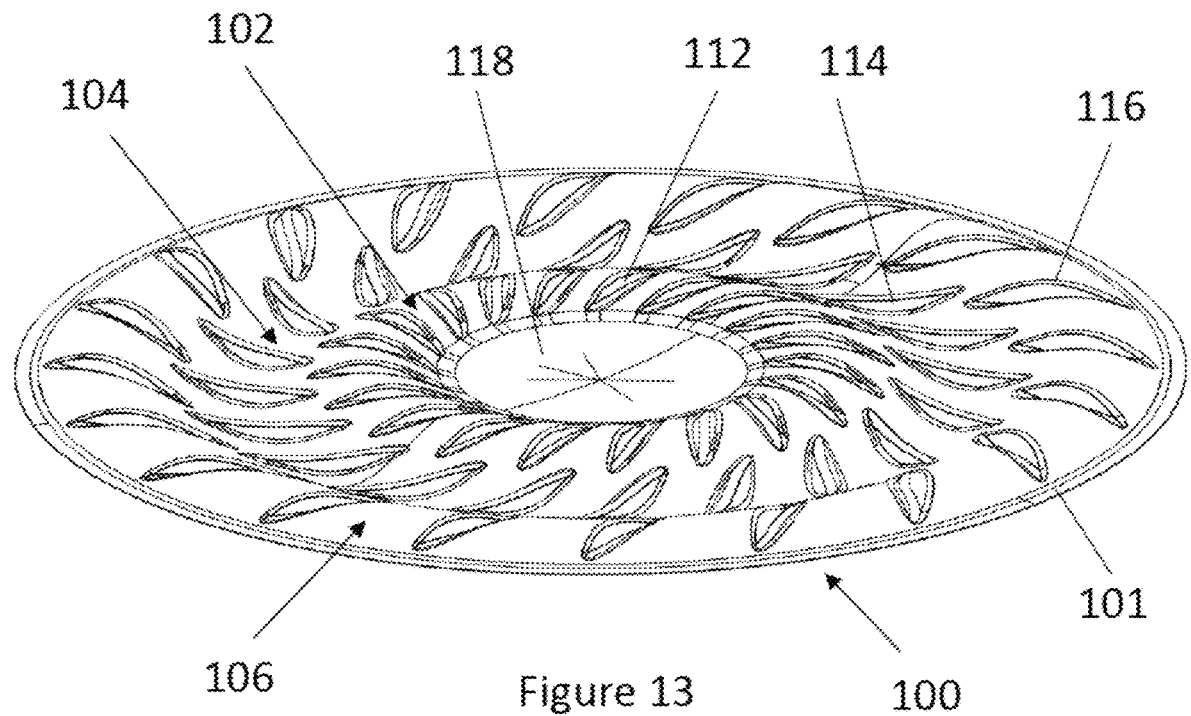
FIG. 13 shows an alternative isometric view of the membrane seen in FIG. 12.

FIG. 12 and FIG. 13 show plan and isometric views respectively of a membrane 100 in accordance with another embodiment the invention. This membrane can be used in any of the hearing protection device embodiments described above or indeed any other such embodiments. The membrane 100 is formed on and supported by a brass ring 101 which extend around the circumference of the membrane. As can be seen more clearly from FIG. 13, the membrane 100 comprises three waves 102, 104, 106. The innermost wave 102 and the outermost wave 106 are 'positive' waves, extending above higher than the centre of the membrane 118. The intervening wave 104 is a 'negative' wave extending lower than height of the centre of the membrane 118.

The membrane 100 also includes three sets of perturbations 112, 114, 116 corresponding to waves 102, 104, 106.

The perturbations 112, 114, 116 reduce stress in the waves 102, 104, 106, allowing the system to vibrate more freely.

The perturbations 112, 114, 116 are spaced evenly around the circumference of their corresponding wave 102, 104, 106. As the same number of perturbations 112, 114, 116 are present on each wave, the density of the perturbations on the innermost wave 102 is the greatest (i.e. their relative spacing is the smallest) whilst the density of the perturbations on the outermost wave 106 is the lowest.

The perturbations 112, 114, 116 extend towards the tangential plane of the centre of the membrane 118. When viewed from the angle shown in FIG. 13, perturbations 112, 116 on the positive waves 102, 104 appear as indentations, whereas perturbations 114 on the negative wave 104 appear as projections. The perturbations 112, 114, 116 are non-radial, diverging from the radius of the membrane 100 by the same angle.

The central portion 118 of the membrane 100 is slightly domed (not visible in Figures). When the membrane is implemented in the device 1 shown in FIG. 1, the piston would be arranged to contact the membrane at its centre 118.

The particular arrangement of waves 102, 104, 106 and perturbations 112, 114, 116 shown in FIGS. 12 and 13 provide a membrane 100 which can vibrate freely when the piston is not touching the membrane and become increasingly stiff when the tension of the membrane is increased by the piston. The arrangement also minimises creep in the membrane 100 at high tensions, which can result in the changes in behaviour of the membrane to vibrations over time.

Figure 14A:
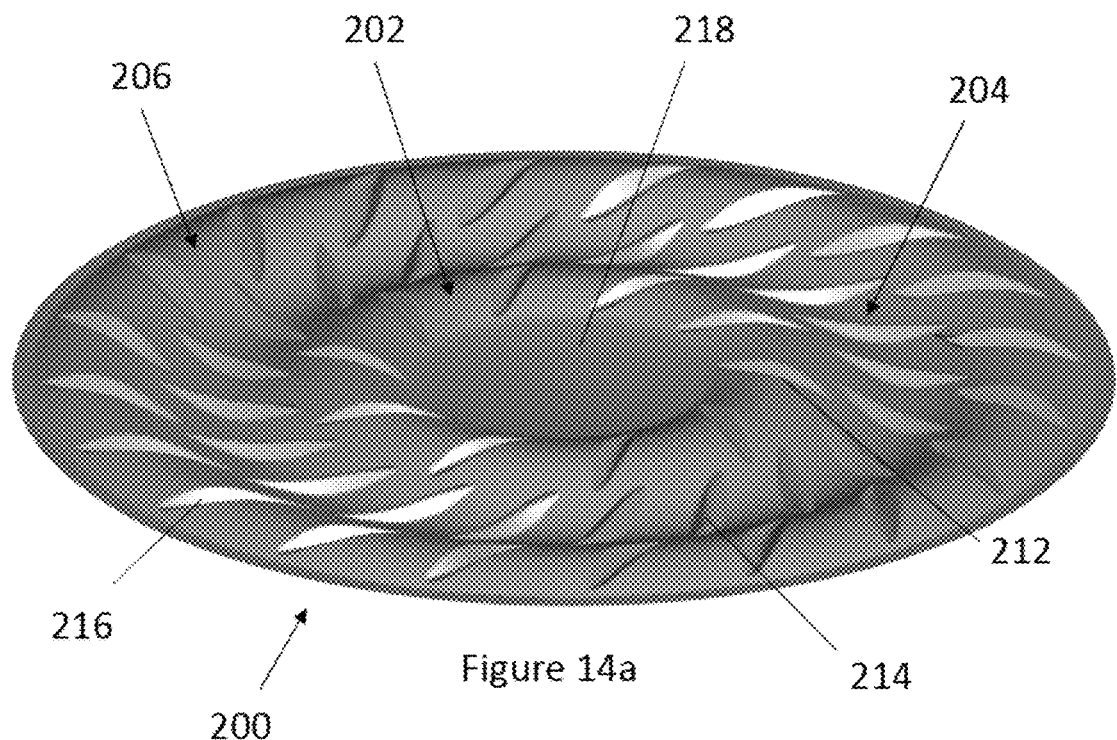
FIGS. 14a and 14b show plan views of membranes in accordance with further embodiments of the present invention.
Figure 14B:
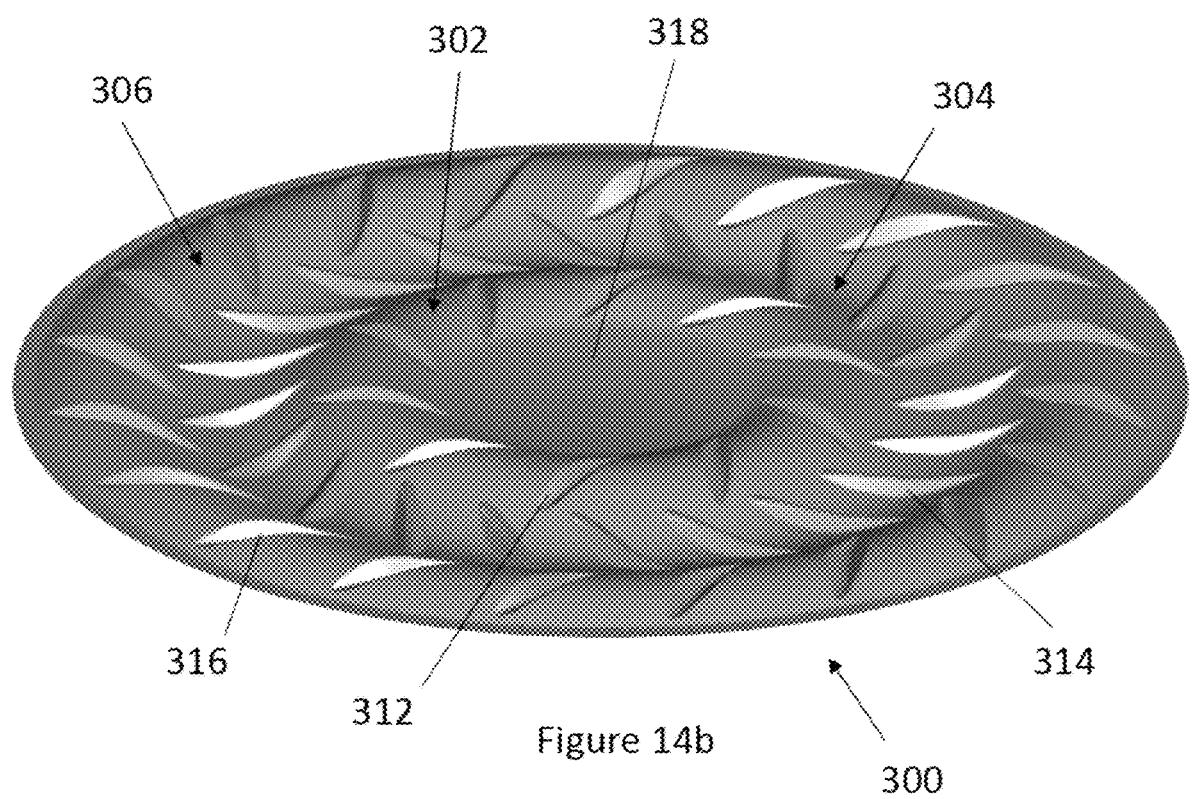

FIGS. 14a and 14b show plan views of membranes in accordance with further embodiments of the present invention. Similar to the membrane 100, shown in FIGS. 12 and 13, the membranes 200, 300 shown in FIGS. 14a and 14b include three waves and perturbations on each wave.

The perturbations in FIGS. 14a and 14b differs from that seen in FIGS. 12 and 13. Membranes 200, 300 shown in FIGS. 14a and 14b have fewer perturbations on the innermost wave 202, 302. The innermost wave 202, 302 comprises ten perturbations, whereas the intervening wave 204, 304 and the outermost wave 206, 306 comprise twenty perturbations.

The membrane 400, shown in FIG. 14b, includes an additional variation in the arrangement of the perturbations. The perturbations on the middle wave 304 are angled in an opposite non-radial direction compared with the perturbations on the innermost wave 302 and the outermost wave 304.

Figure 15A:
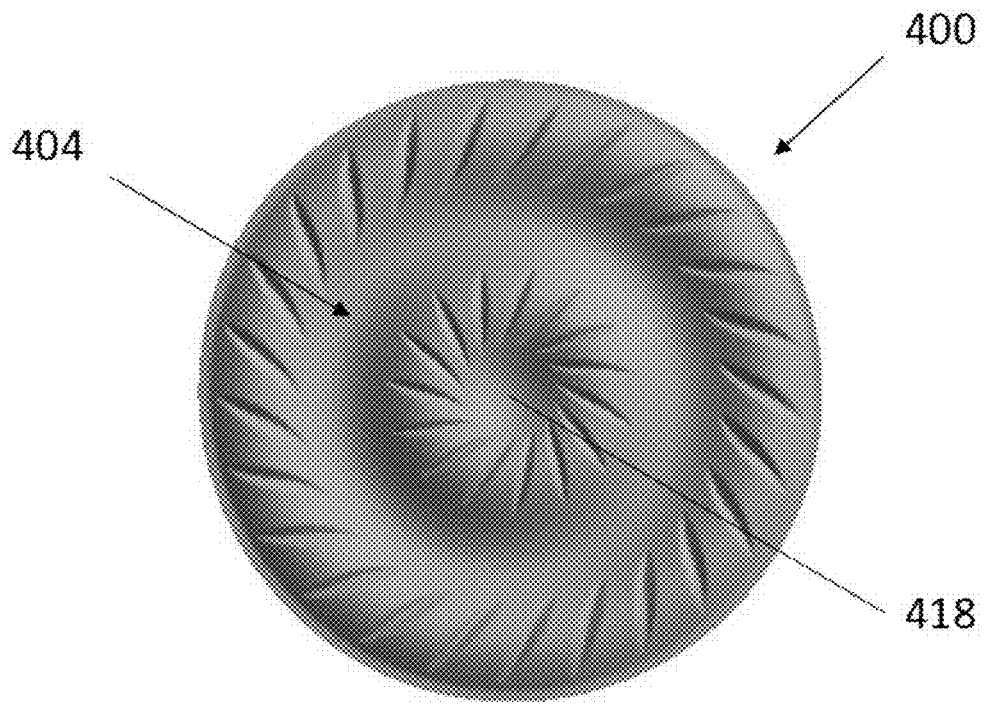
FIGS. 15a-15c show views of membranes in accordance with further embodiments of the present invention.
Figure 15B:
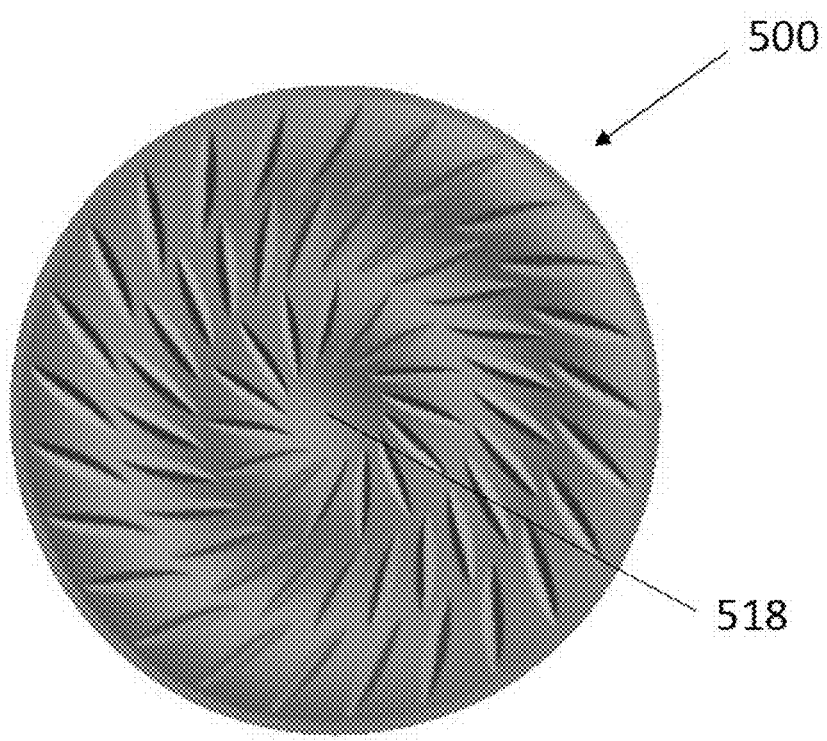
Figure 15C:
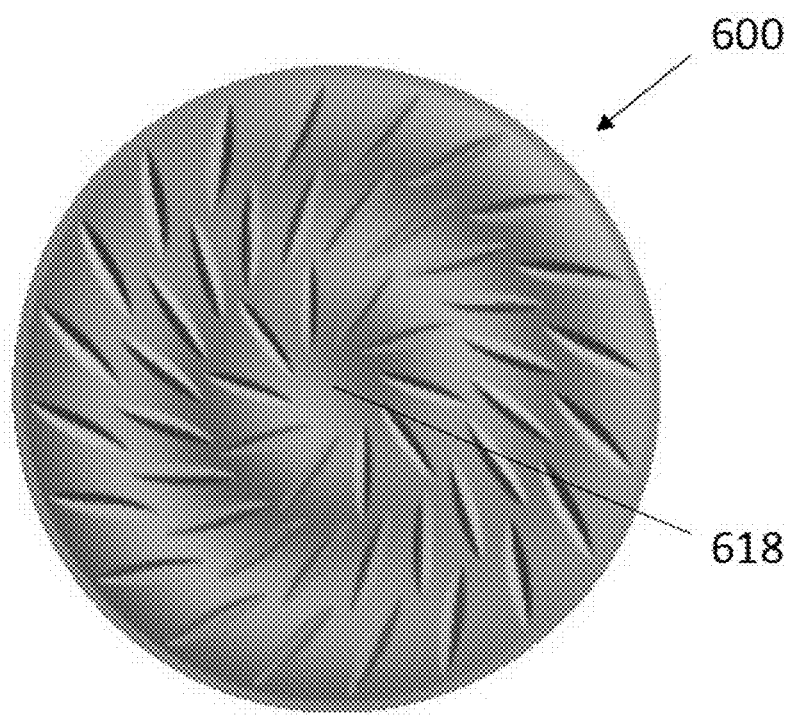

FIGS. 15a to 15c show views of membranes in accordance with other possible embodiments of the present invention. For example the central portions 418, 518, 618 of the membranes 400, 500, 600 shown in FIGS. 15a to 15c have a smaller diameters compared with those seen in FIGS. 12 to 14b.

The membrane 400 shown in FIG. 15a has no perturbations on the middle wave 404. The innermost wave on the membrane 400 has fifteen perturbations, whereas the outermost wave has twenty five perturbations.

The membrane 500 shown in FIG. 15b has perturbations on all three waves. The innermost wave on the membrane 500 has fifteen perturbations, whereas the intervening and outermost wave have twenty five perturbations.

The membrane 600 shown in FIG. 15c has a similar arrangement of perturbations to that shown in FIG. 14a.

Of course there are many other variants of waves and perturbations possible in accordance with the invention.

The invention claimed is:

1. A device, for insertion into an ear canal of a mammalian subject, comprising:
   a body, having a sound path extending therethrough;
   a tensioned membrane in the sound path comprising at least one corrugation; and
   an adjustable member arranged to bear against the tensioned membrane to adjust the tension of the tensioned membrane and thereby to alter an acoustic response of the sound path.

2. The device as claimed in claim 1, wherein the at least one corrugation is arranged on the tensioned membrane such that the adjustable member does not contact the at least one corrugation.

3. The device as claimed in claim 1, wherein the adjustable member is arranged to contact the tensioned membrane in a geometric centre of the tensioned membrane.

4. The device as claimed in claim 1, wherein the tensioned membrane comprises a plurality of waves, each wave comprising a corrugation in the form of a circular ridge or indentation.

5. The device as claimed in claim 4, wherein the plurality of waves comprise alternating circular indentations and ridges.

6. The device as claimed in claim 4, wherein the tensioned membrane comprises three waves.

7. The device as claimed in claim 4, wherein each wave comprises a plurality of circumferentially spaced perturbations.

8. The device as claimed in claim 7, wherein the circumferentially spaced perturbations extend in an opposite direction to the corresponding wave on which they are formed.

9. The device as claimed in claim 7, wherein the circumferentially spaced perturbations are non-radial.

10. The device as claimed in claim 7, wherein each wave comprises the same number of circumferentially spaced perturbations.

11. The device as claimed in claim 1, wherein the adjustable member comprises a compressible portion.

12. The device as claimed in claim 11, wherein the compressible portion is formed from a layer of inherently compressible material.

13. The device as claimed in claim 11, wherein the compressible portion of the adjustable member is arranged to contact the surface of the tensioned membrane.

14. The device as claimed in claim 1, wherein the device comprises a first adjustable acousto-mechanical portion comprising an adjustable channel forming at least part of the sound path and a second adjustable acousto-mechanical portion arranged acoustically in series with the first acousto-mechanical portion comprising the tensioned membrane, and an adjustment arrangement comprising said adjustable member for simultaneously adjusting the first and the second acousto-mechanical portions to alter the acoustic response of the at least one sound path.

15. The device as claimed in claim 1, wherein the adjustable member has a position wherein the adjustable member is not in contact with the tensioned membrane.

16. The device as claimed in claim 1, wherein the adjustable member has a plurality of positions wherein the adjustable member is in contact with the tensioned membrane.

17. The device as claimed in claim 1, further comprising a user operable member arranged to rotate the adjustable member relative to a central axis thereof for adjusting a position of the adjustable member.

18. The device as claimed in claim 17, further comprising an arrangement for converting rotational movement of the user operable member to axial movement of the adjustable member.

19. The device as claimed in claim 1, wherein the adjustable member comprises a base which contacts the tensioned membrane in use and which comprises a low friction coating or layer.

20. The device as claimed in claim 1, wherein a or the centre of the tensioned membrane is domed.

21. The device as claimed in claim 1, wherein the tensioned membrane comprises part of an adjustable acousto-mechanical portion of the device and wherein the device comprises a further adjustable acousto-mechanical portion comprising an adjustable channel forming at least part of the sound path, and the device further comprises an adjustment arrangement for adjusting the further acousto-mechanical portion.

22. The device as claimed in claim 21, wherein the adjustment arrangement is configured to adjust a length and/or width of the adjustable channel.

23. The device as claimed in claim 21, wherein the adjustment arrangement comprises a common actuator arranged to adjust both acousto-mechanical portions simultaneously.

24. The device as claimed in claim 21, wherein the channel is defined by a space between a wall of a cavity within the body and a piston arranged in the cavity, wherein adjustment of the channel is achieved by moving the piston relative to the cavity.

25. The device as claimed in claim 24, wherein the cavity and the piston each have a frusto-conical shape such that the adjustable channel has the form of a frusto-conical shell.

26. The device as claimed in claim 24, wherein the piston is provided by the adjustable member.

27. The device as claimed in claim 24, wherein the piston is arranged to move axially within the cavity and the device comprises at least one resilient member arranged to bias the piston into or out of the cavity, wherein the adjustment arrangement comprises an actuation member arranged to drive the piston against the resilient bias axially out of or into the cavity respectively.

28. A device, for insertion into an ear canal of a mammalian subject, comprising:
- a body, having a sound path extending therethrough;
- a tensioned membrane in the sound path; and
- an adjustable member comprising a compressible portion and arranged to bear against the tensioned membrane to adjust the tension of the tensioned membrane and thereby to alter an acoustic response of the sound path.

* * * * *